United States Patent
Park et al.

(10) Patent No.: US 10,856,842 B2
(45) Date of Patent: Dec. 8, 2020

(54) ULTRASONIC WAVE GENERATING DEVICE AND PROCEDURE METHOD USING THE SAME

(71) Applicant: ATTIBE Beauty Co., LTD., Seoul (KR)

(72) Inventors: Rae Eun Park, Seongnam-si (KR); Hyung Chel Kim, Yongin-si (KR); Sung Won Lee, Yongin-si (KR)

(73) Assignee: ATTIBE Beauty Co., LTD., Seoul (KR)

( * ) Notice: Subject to any disclaimer, the term of this patent is extended or adjusted under 35 U.S.C. 154(b) by 464 days.

(21) Appl. No.: 15/529,767

(22) PCT Filed: Mar. 11, 2015

(86) PCT No.: PCT/KR2015/002331
§ 371 (c)(1),
(2) Date: May 25, 2017

(87) PCT Pub. No.: WO2016/085051
PCT Pub. Date: Jun. 2, 2016

(65) Prior Publication Data
US 2017/0303895 A1 Oct. 26, 2017

(30) Foreign Application Priority Data

Nov. 26, 2014 (KR) .................. 10-2014-0166393
Nov. 26, 2014 (KR) .................. 10-2014-0166394
Feb. 25, 2015 (KR) .................. 10-2015-0026533

(51) Int. Cl.
*A61B 8/00* (2006.01)
*A61N 7/02* (2006.01)
(Continued)

(52) U.S. Cl.
CPC .................. *A61B 8/44* (2013.01); *A61N 7/02* (2013.01); *G01S 7/521* (2013.01);
(Continued)

(58) Field of Classification Search
None
See application file for complete search history.

(56) References Cited

U.S. PATENT DOCUMENTS 4,732,156 A * 3/1988 Nakamura ............... A61B 8/12
600/101
5,130,868 A * 7/1992 Ida ......................... G11B 5/024
360/57
(Continued)

FOREIGN PATENT DOCUMENTS

DE         3619195 A1    1/1987
JP         S61-293439    12/1986
(Continued)

OTHER PUBLICATIONS

Search Report, dated May 24, 2018, issued from European Property Office (EPO) in corresponding European Patent Application No. 15862354.6, 9pp.
(Continued)

*Primary Examiner* — Patricia J Park
*Assistant Examiner* — Younhee Choi
(74) *Attorney, Agent, or Firm* — Novick, Kim & Lee, PLLC; Sang Ho Lee

(57) ABSTRACT

An ultrasonic wave generating device includes a housing to seal an inside of a cartridge; a transducer to generate ultrasonic waves and disposed in the housing; a rotational force applying unit to receive a rotational force from an outside of the housing and perform a rotational motion; a conversion unit to convert the rotational motion of the rotational force applying unit into a rectilinear motion and
(Continued)

provide the rectilinear motion to the transducer; and a controller to control an ultrasonic wave generating operation of the transducer.

11 Claims, 17 Drawing Sheets

(51) Int. Cl.
    *G01S 7/521*     (2006.01)
    *A61B 17/00*     (2006.01)
    *A61N 7/00*     (2006.01)
(52) U.S. Cl.
    CPC ............ *A61B 2017/00477* (2013.01); *A61B 2017/00734* (2013.01); *A61N 2007/0008* (2013.01); *A61N 2007/0034* (2013.01)

(56) References Cited

U.S. PATENT DOCUMENTS

| | | | | |
|---|---|---|---|---|
| 8,523,849 B2 * | 9/2013 | Liu | ...................... | A61B 18/203 606/9 |
| 2005/0154431 A1 | 7/2005 | Quistgaard | | |
| 2007/0232913 A1 | 10/2007 | Lau et al. | | |
| 2012/0016239 A1 * | 1/2012 | Barthe | ................. | A61B 8/0858 600/439 |

FOREIGN PATENT DOCUMENTS

| | | |
|---|---|---|
| KR | 10-2007-0065332 A | 6/2007 |
| KR | 2011-0091831 | 8/2011 |
| KR | 10-2012-0100049 A | 9/2012 |
| KR | 10-1191347 B | 10/2012 |
| KR | 10-1307551 B | 9/2013 |
| KR | 10-2014-0067482 A | 6/2014 |
| WO | 2014-129732 A1 | 8/2014 |
| WO | 2014-157787 A1 | 10/2014 |

OTHER PUBLICATIONS

International Search Report dated Jul. 13, 2015, corresponding to PCT/KR2015/002331.
Office Action and English Translation for Japanese Patent Application No. 2017-528572 dated Nov. 20, 2018; 8 pages.

* cited by examiner (a)

(b)

20

20

(a)

(b)

ULTRASONIC WAVE GENERATING DEVICE AND PROCEDURE METHOD USING THE SAME

CROSS-REFERENCE TO RELATED APPLICATIONS

This application is a filing under 35 U.S.C. § 371 of International Patent Application PCT/KR2015/002331 filed Mar. 11, 2015, and claims the priority to and the benefit of KR 10-2014-0166394 filed Nov. 26, 2014; 10-2014-0166393 filed Nov. 26, 2014; and 10-2015-0026533 filed Feb. 25, 2015. These applications are incorporated by reference herein in their entirety.

FIELD

The present disclosure relates to an ultrasonic wave generating device and a procedure method.

BACKGROUND

The statements in this section merely provide background information related to the present disclosure and may not constitute prior art.

Recently, various procedures for skin care or obesity procedure have been developed, and interest in noninvasive procedures among these various procedures is increasing.

Meanwhile, ultrasonic waves are widely used for noninvasive procedures, and among the procedures, ultrasonic wave medical devices using high intensity focused ultrasound (HIFU) have been recently spotlighted. For example, ultrasonic wave medical devices that perform procedures for skin care, such as face lifting or skin tightening, in a noninvasive manner by radiating HIFU into an inside of a skin tissue, or ultrasonic wave medical devices that perform procedures for obesity procedure by radiating HIFU onto a subcutaneous layer and decomposing an adipose tissue by burning or melting in a noninvasive manner have been suggested.

Related pieces of literature include U.S. Patent Publication No. 2007-0232913 A1, Korean Patent Publication Nos. KR 10-2011-0091831 A1, and KR 10-2007-0065332 A1.

SUMMARY

The present disclosure is directed to providing a technique capable of at least one of improvements in efficiency of a procedure, extension of a service life, miniaturization of a device, improvements in economic feasibility, and improvements in stability or reliability.

One aspect of the present disclosure provides an ultrasonic wave generating device including: a housing configured to seal an inside of a cartridge; a transducer disposed in the housing and configured to generate ultrasonic waves; a rotational force applying unit configured to receive a rotational force from an outside of the housing and perform a rotational motion; a conversion unit configured to convert the rotational motion of the rotational force applying unit into a rectilinear motion and provide the rectilinear motion to the transducer; and a controlling means configured to control an ultrasonic wave generating operation of the transducer.

The ultrasonic wave generating device may further include an outer rotating unit disposed outside the housing and connected to the rotational force applying unit by magnetism.

The conversion unit may include a driving joint connected to the rotational force applying unit and configured to rotate; and a driven joint fixed to the transducer and configured to perform a forward and backward rectilinear motion based on the rotational motion of the driving joint.

The ultrasonic wave generating device may further include a position detection unit configured to detect a position of the transducer, wherein the controlling means may control the transducer not to generate the ultrasonic waves based on a signal output from the position detection unit when the transducer is within a predetermined distance from a previous position at which the ultrasonic waves are generated.

The ultrasonic wave generating device may further include a sensing means configured to sense at least one of an amount of a fluid, an inclination of a water surface of the fluid, or an inclination of the cartridge, wherein a fluid used to transmit the ultrasonic wave may be filled in the housing, and the controlling means may control the transducer to stop generation of the ultrasonic waves when at least one of the amount of the fluid, the inclination of the water surface of the fluid, or the inclination of the cartridge deviates from a predetermined range.

The conversion unit may include a cylindrical cam having a cylindrical shape, including a groove portion or a protrusion with a spiral shape provided at an outer circumferential surface thereof, and having one end coupled to the rotational force applying unit; a guide portion provided in parallel to a rotating shaft of the cylindrical cam; and a transfer member having a first side fixed to the transducer and a second side inserted into the groove portion, wherein the protrusion is inserted into the second side of the transfer member, and the transfer member performs a rectilinear motion along the guide portion.

The position detection unit may include a first magnet unit provided in one of the cylindrical cam and the housing; and a first sensor provided in the cartridge and configured to detect a position of the first magnet unit.

The position detection unit may include a second magnet unit provided in the transfer member or the transducer; and a second sensor provided in the cartridge to face the second magnet unit and configured to detect a position of the second magnet unit.

The transfer member may perform a rectilinear motion between a first reference point and a second reference point, and the second sensor may be provided at a position facing the second magnet unit when the transfer member is disposed at the first reference point, and at a position facing the second magnet unit when the transfer member is disposed at the second reference point.

Another aspect of the present disclosure provides an ultrasonic wave generating apparatus including: a procedure handpiece for a manipulation by a practitioner; a cartridge configured to be attached to or detached from the procedure handpiece and including a cartridge body; a transducer provided in a cartridge body and configured to generate a thermal lesion including high intensity focused ultrasound (HIFU); an outer rotating unit provided in the procedure handpiece; a rotational force applying unit provided in the cartridge and connected to the outer rotating unit by magnetism when an outer wall of the cartridge is disposed between the outer rotating unit and the rotational force applying unit; a conversion unit configured to convert a rotational motion of the rotational force applying unit into a rectilinear motion and provide the rectilinear motion to the transducer; a position detection unit configured to detect a position of the transducer; and a controlling means configured to control an ultrasonic wave generating operation of the transducer based on a signal output from the position detection unit.

The conversion unit may include a cylindrical cam having a cylindrical shape, including a groove portion or a protrusion with a spiral shape provided at an outer circumferential surface thereof, and having a first end coupled to the rotational force applying unit; a guide portion provided in parallel to a rotating shaft of the cylindrical cam; and a transfer member having a first side fixed to the transducer and a second side inserted into the groove portion, wherein the protrusion is inserted into the second side of the transfer member, and the transfer member is configured to perform a rectilinear motion along the guide portion.

The position detection unit may include a first magnet unit provided on the second end of the cylindrical cam; and a first sensor provided in the cartridge to face the first magnet unit and configured to detect a position of the first magnet unit.

The position detection unit may include a second magnet unit provided in the transfer member or the transducer; and a second sensor provided in the cartridge to face the second magnet unit and configured to detect a position of the second magnet unit, and the transfer member may perform a rectilinear motion between a first reference point and a second reference point, and the second sensor may be provided at a position facing the second magnet unit when the transfer member is disposed at the first reference point, and at a position facing the second magnet unit when the transfer member is disposed at the second reference point.

The ultrasonic wave generating device may further include a sensing means configured to sense at least one of an amount of a fluid, an inclination of a water surface of the fluid, or an inclination of the cartridge, wherein the fluid may be filled in the housing, and the controlling means turns off the transducer when the inclination of the cartridge deviates from a predetermined range.

Another aspect of the present disclosure provides a procedure method using an ultrasonic wave generating device, the method including: performing a procedure by generating thermal lesions of high intensity focused ultrasound (HIFU) at a predetermined depth of a skin tissue in a noninvasive manner using the above-described ultrasonic wave generating device, wherein the transducer is moved between a first reference point and a second reference point; sensing whether the transducer is within a predetermined distance from a previous position at which the HIFU is generated using the transducer while the transducer is moved between the first reference point and the second reference point; and controlling the transducer not to generate the HIFU when the transducer is within the predetermined distance from the previous position at which the HIFU is generated.

The transducer may perform a rectilinear motion between the first reference point and the second reference point by receiving a rotational motion of a cylindrical cam having a cylindrical shape and being rotated, and the sensing of whether the transducer is within a predetermined distance from the previous position at which the HIFU is generated using the transducer may be performed by detecting a rotation degree of the cylindrical cam.

The method may further include, when the transducer is disposed at the first reference point or the second reference point, stopping movement of the transducer.

The method may further include adjusting a distance between the thermal lesions by controlling a rotational speed of a cylindrical cam, wherein the transducer may perform a rectilinear motion between the first reference point and the second reference point by receiving a rotational motion of the cylindrical cam having a cylindrical shape and being rotated.

According to an embodiment of the present disclosure, an ultrasonic wave-emitting unit can rectilinearly move even in a state in which a cartridge is fixed in a predetermined position so that manpower or time required for a procedure can be reduced. Thus, efficiency of a procedure using an ultrasonic wave generating device can be improved.

In addition, because the ultrasonic wave-emitting unit can reciprocate in a state in which an inside and an outside of the cartridge are blocked so that loss of a fluid to be filled in the cartridge can be decreased, a cartridge replacement period or a fluid filling period is extended, and maintenance costs can be reduced.

In addition, a driving device, such as a motor, is provided in a procedure handpiece on which several cartridges can be alternately mounted so that several cartridges can share the driving device and price competitiveness of a procedure apparatus including the ultrasonic wave generating device can be improved.

In addition, because a position of an ultrasonic wave generating unit can be precisely checked and an ultrasonic wave generating operation can be controlled in consideration of the position of the ultrasonic wave generating unit, stability of a procedure can be improved.

According to an embodiment of the present disclosure, the amount of the fluid filled in the cartridge can be detected and a situation in which the fluid is insufficient can be rapidly recognized by a practitioner, and a countermeasure, such as filling the fluid or replacing the cartridge, can be rapidly taken so that efficiency of a procedure can be improved. In addition, a risk of damage to the cartridge which may occur when the cartridge is continuously used in a state in which the fluid is insufficient can be reduced.

In addition, no ultrasonic waves are generated in a situation in which an inclination of the cartridge is detected as not being proper so that safety can be improved.

In addition, the inclination of the cartridge can be detected using only a fluid contact sensor without an additional tilt sensor.

DRAWINGS

In order that the disclosure may be well understood, there will now be described various forms thereof, given by way of example, reference being made to the accompanying drawings, in which.

Figure 1:
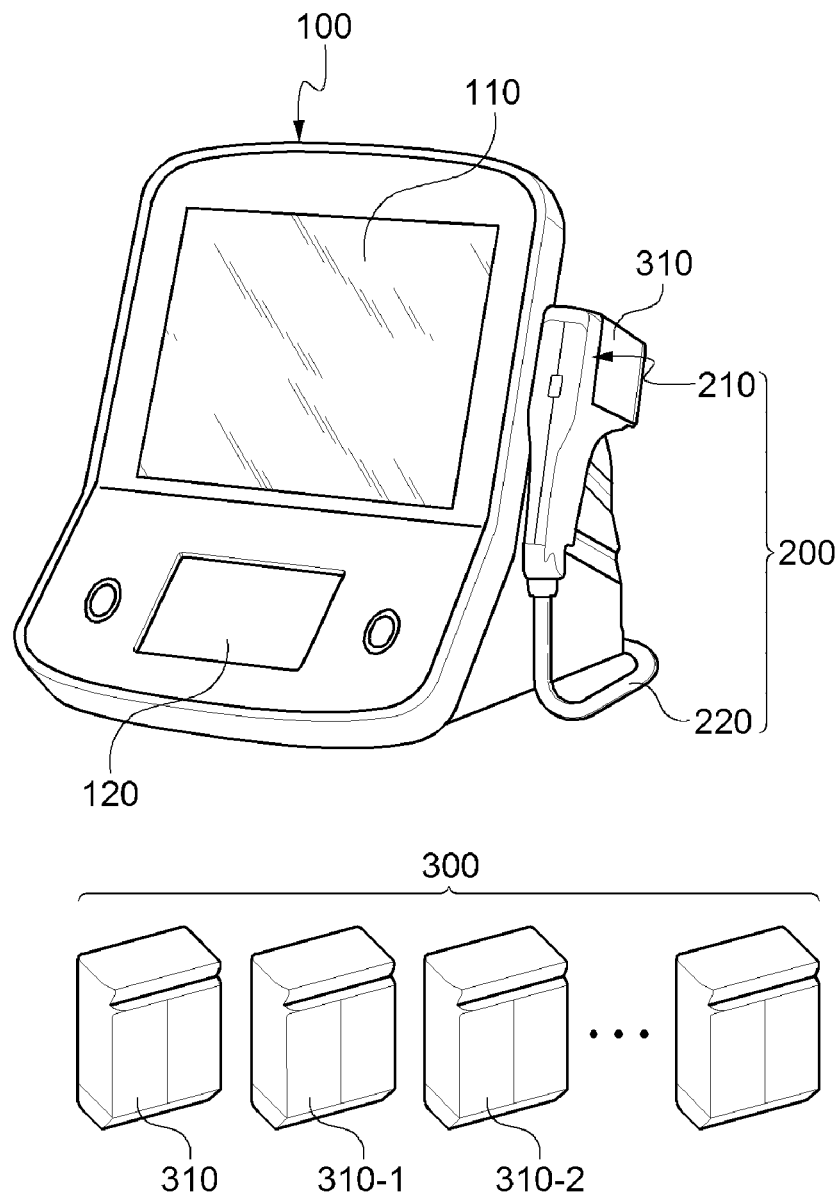
FIG. 1 is a perspective view schematically illustrating an ultrasonic wave generating device according to an embodiment of the present disclosure.

The drawings described herein are for illustration purposes only and are not intended to limit the scope of the present disclosure in any way.

DETAILED DESCRIPTION

Referring to FIGS. 1 to 5, an ultrasonic wave generating device according to an embodiment of the present disclosure may be a medical device that performs various procedures using high intensity focused ultrasound (HIFU).

In an embodiment, the ultrasonic wave generating device may perform two or more different procedures. For example, the ultrasonic wave generating device may perform a procedure such as noninvasive face lifting or skin tightening and noninvasive reduction or removal of a subcutaneous layer.

The HIFU may be used to form a thermal lesion 12 by focusing ultrasonic wave onto one focus point. The thermal lesion 12 may be a thermal focus point in a high temperature state of approximately 60° C. or higher.

Thus, the ultrasonic wave generating device may perform face lifting or skin tightening by forming the thermal lesion 12 on a dermal layer, a fascial layer, or a SMAS layer spaced approximately 1.5 to 4.5 mm apart from a surface of the skin, or may perform a fat reduction or removal procedure by forming the thermal lesion 12 on a subcutaneous layer spaced approximately 6.0 to 15.0 mm apart from the surface of the skin.

Meanwhile, an ultrasonic wave generating device 10 according to an embodiment of the present disclosure may include an equipment body 100, a handpiece assembly 200, and a cartridge set 300.

The equipment body 100 may provide procedural information to a practitioner (not shown) and may help the practitioner to operate or manipulate the ultrasonic wave generating device 10. For example, the equipment body 100 may include a display unit 110 for displaying procedural information of the practitioner and a controller 120 that allows the practitioner to operate or control the ultrasonic wave generating device 10. Here, the controller 120 may be a touch screen or the like.

The handpiece assembly 200 may include a procedure handpiece 210 and a connection cable 220. The procedure handpiece 210 is used to radiate HIFU onto a procedural subject, and may have a hand-held shape so as to improve convenience of user manipulation. For example, the procedure handpiece 210 may include a handle unit 212 through which the practitioner can grip the handpiece 210. A switch 212a through which the practitioner controls an ultrasonic wave radiating operation may be provided at a top end of the handle unit 212. The connection cable 220 may be used to electrically or physically connect the procedure handpiece 210 to the equipment body 100. One end of the connection cable 220 may be connected to the procedure handpiece 210, and the other end of the connection cable 220 having a connecting type may be detachably connected to the equipment body 100.

In an embodiment, the cartridge set 300 may be a set including a plurality of cartridges. For example, the cartridge set 300 may include first through third cartridges 310, 310-1, and 310-2 having different procedure types and procedure conditions. Each of the first through third cartridges 310, 310-1, and 310-2 may be configured to be attached to or detached from the procedure handpiece 210. For example, functions of the first cartridge 310 and the second cartridge 310-1 are classified according to an obese state or a procedure part of an obese patient. In detail, conditions such as a radiation intensity and a radiation depth of the HIFU may be different. Also, the third cartridge 310-2 may be set to a condition of a radiation intensity and a radiation depth of the HIFU for performing a face lifting or skin tightening procedure. Furthermore, a cartridge for performing a procedure for removing a tumor or cancerous tissue may also be used.

In more detail, a transducer 314 provided inside the cartridge set 300 may be moved in forward and backward directions so that each of the first through third cartridges 310, 310-1, and 310-2 may have a procedure region of approximately 40.0 to 100.0 mm. In this case, the transducer 314 may radiate the HIFU while being moved within the range. Meanwhile, when a forward and backward movement range of the transducer 314 is approximately 40.0 mm or less, the procedure region is small and a procedure time can be greatly extended. Also, because the transducer 314 is set to radiate the HIFU to a predetermined depth and the subcutaneous layer is spread to be curved in both-side directions of the human navel, when the forward and backward movement range of the transducer 314 exceeds approximately 100.0 mm, an initial HIFU radiation depth and a final HIFU radiation depth with respect to a subcutaneous layer may be different. As a result, a risk of the HIFU being radiated in a region that deviates from the subcutaneous layer may be greatly increased. Thus, the transducer 314 may be set to be moved forward and backward in the range of approximately 40.0 to 100.0 mm, or, in a range of approximately 60.0 to 80.0 mm, which may be advantageous in securing procedure safety and a reduction in a procedure time.

As described above, the ultrasonic wave generating device 10 according to an embodiment of the present disclosure includes the cartridge set 300 including the first through third cartridges 310, 310-1, and 310-2 having different procedure types or procedure conditions, and then selects a cartridge suitable for a procedure type or procedure condition from the first through third cartridges 310, 310-1, and 310-2 and mounts the cartridge on the procedure handpiece 210 so that a procedure customized for a patient can be performed.

Meanwhile, in the ultrasonic wave generating device 10 according to an embodiment of the present disclosure, a rotational force outside the first through third cartridges 310, 310-1, and 310-2 may be transferred to an inside of the cartridges, and the transducer 314 may be moved in a rectilinear direction by the rotational force.

In an embodiment, the first cartridge 310 may include a rotational force applying unit 350 provided inside a region surrounded by the housing 312, a conversion unit, and the transducer 314.

The rotational force applying unit 350 performs a function of applying a rotational force provided from an outside of the housing 312. In an example, the rotational force may be transferred from an outer rotating unit 233 that performs a rotating motion outside the housing 312 to the rotational force applying unit 350. Here, the rotational force applying unit 350 and the outer rotating unit 233 are not in direct contact with each other and face each other in a state in which the housing 312 is disposed therebetween. The rotational force applying unit 350 and the outer rotating unit 233 may be connected to each other due to magnetism. To this end, the rotational force applying unit 350 and the outer rotating unit 233 may be formed of a magnetic material or may include a magnetic material. In addition, a region between the rotational force applying unit 350 of the housing 312 and the outer rotating unit 233 is formed of a non-magnetic material so that a reduction in a magnetic coupling force between the rotational force applying unit 350 and the outer rotating unit 233 can be minimized. Of course, although the entire housing 312 may be formed of the non-magnetic material, when the housing 312 is not the region between the rotational force applying unit 350 and the outer rotating unit 233, the housing 312 may be formed of a magnetic material.

In an embodiment, the rotational force applying unit 350 and the outer rotating unit 233 may have a general disc shape. Thus, the magnetic coupling force between the rotational force applying unit 350 and the outer rotating unit 233 can be maximized, a minimum of space is desired, and a frictional force therebetween can be reduced.

In addition, a concave portion is provided in the housing 312, and a part of the rotational force applying unit 350 and the outer rotating unit 233 is inserted into the concave portion so that the rotational force applying unit 350 and the outer rotating unit 233 can be stably supported and can smoothly perform a rotational motion.

In addition, a member such as a bearing may be provided between the rotational force applying unit 350 and the housing 312 and between the outer rotating unit 233 and the housing 312 so that frictional forces therebetween can be reduced and a smooth rotational motion can be performed through the bearings.

In an embodiment, the outer rotating unit 233 may be connected to a rotating shaft 232 of a motor 231. The motor 231, the rotating shaft 232, and the outer rotating unit 233 may be provided in the procedure handpiece.

Figure 2:
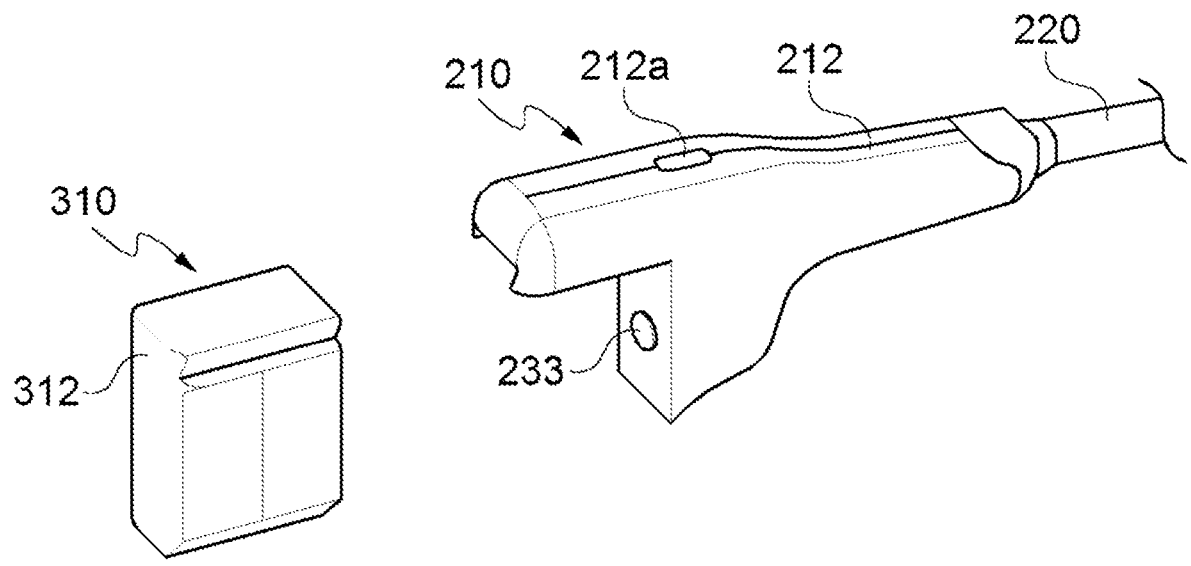
FIG. 2 is a view for explaining a combination relationship between a procedure handpiece and a cartridge illustrated in FIG. 1.
Figure 2:
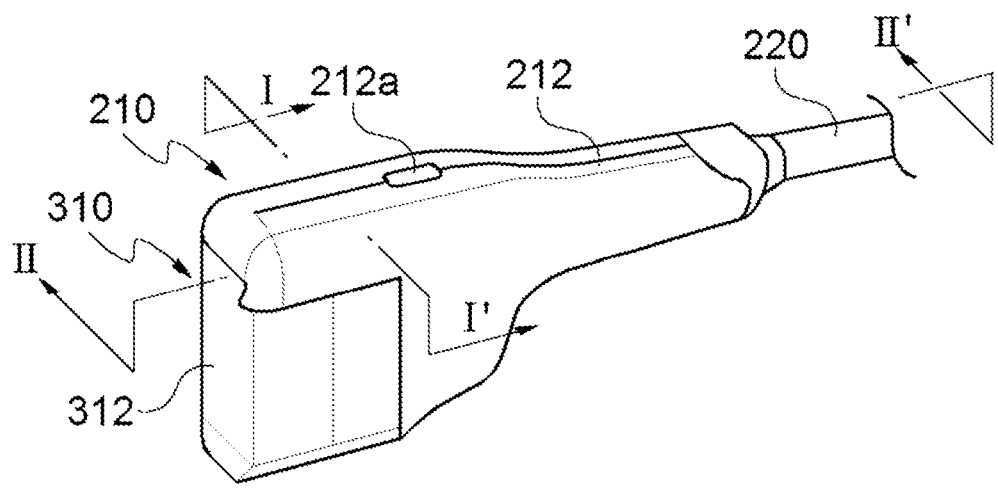

Here, referring to FIG. 2, the first cartridge 310 may be coupled to the procedure handpiece. In this case, the outer rotating unit 233 is disposed at a portion at which the first cartridge 310 and the procedure handpiece are in contact with each other. As illustrated in FIG. 2, at least a part of the outer rotating unit 233 protrudes toward an outside of the procedure handpiece and is inserted into the concave portion of the housing 312 so that a magnetic coupling force between the outer rotating unit 233 and the rotational force applying unit 350 can be increased. Of course, although not shown, a surface of the housing 312 with which the rotational force applying unit 350 is in contact protrudes in a direction of the outer rotating unit 233, and a protruding portion thereof may be inserted into the inside of the procedure handpiece.

Meanwhile, the conversion unit is provided between the rotational force applying unit 350 and the transducer 314 and performs a function of converting the rotational motion of the rotational force applying unit 350 into a rectilinear motion and providing the rectilinear motion to the transducer 314. Thus, the transducer 314 may be moved in the rectilinear direction from an inside of the first cartridge 310.

In an embodiment, the conversion unit may include a driving joint 340 that performs a rotational motion and a driven joint 330 that performs a rectilinear motion. For example, the driving joint 340 is constituted by forming a groove portion 341H having a spiral shape in a surface of a cylindrical cam 341 having a cylindrical shape and may perform the rotational motion, and the driven joint 330 is constituted by moving a transfer member 331 coupled to a protrusion 332 inserted into the groove portion 341H of the cylindrical cam 341 in the rectilinear direction along a guide portion 333. Although not shown, protrusions having a spiral shape may be formed on the surface of the cylindrical cam 341, and the groove portion 341H may be inserted into the protrusion 332 in the transfer member 331.

In addition, the transducer 314 is fixed to the transfer member 331 so that the transducer 314 can be moved in the rectilinear direction with the transfer member 331 according to movement of the transfer member 331 in the rectilinear direction.

Figure 4:
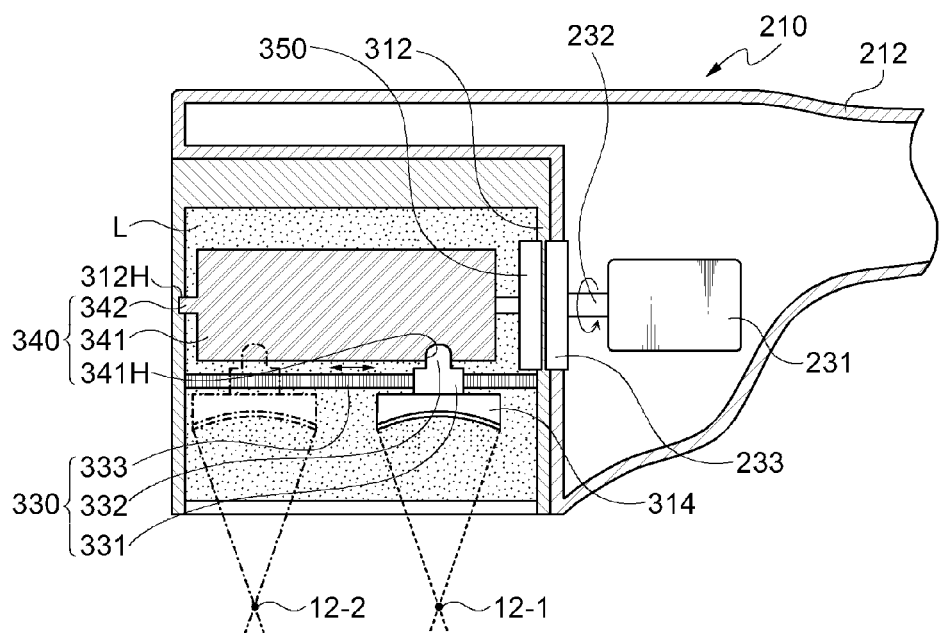
FIG. 4 is a view schematically illustrating a cut surface taken along line II-II' of FIG. 2.
Figure 5:
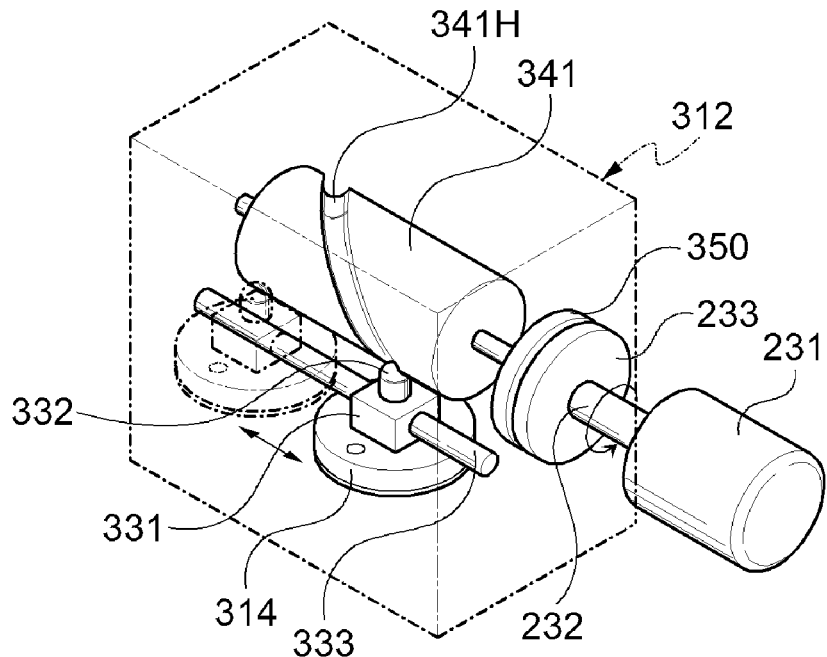
FIG. 5 is a perspective view for explaining primary parts of an ultrasonic wave generating device according to an embodiment of the present disclosure.

In an embodiment, one end of the cylindrical cam 341 is connected to the rotational force applying unit 350. The other end of the cylindrical cam 341 may be rotatably coupled to the housing 312. That is, as illustrated in FIG. 4, a concave groove is provided in the housing 312, a shaft protrusion 342 is provided on the other end of the cylindrical cam 341, and the shaft protrusion 342 is inserted into the concave groove so that the cylindrical cam 341 can be rotatably coupled to the housing 312. Thus, when the rotational force applying unit 350 receives the rotational force from the outer rotating unit 233 and performs a rotational motion, the cylindrical cam 341 can perform a rotational motion.

In an embodiment, the groove portion 341H provided on the surface of the cylindrical cam 341 starts at one side of the cylindrical cam 341, passes through to the other side of the cylindrical cam 341, and returns to the one end of the cylindrical cam 341 to form one round circle. In this case, when the cylindrical cam 341 rotates by 360 degrees, the transfer member 331 and the transducer 314 can perform a rectilinear motion, a so-called rectilinear reciprocating motion, to advance along the guide portion 333 and return to original positions thereof. In this case, a rotational speed of the cylindrical cam 341 may be adjusted in consideration of a rectilinear reciprocating speed of the transducer 314, and a rotational speed of the above-described motor 231 may be controlled, or a rotational speed may be controlled by including a gear (not shown) between the rotating shaft 232 of the motor 231 and the outer rotating unit 233.

In another embodiment, the groove portion 341H provided on the surface of the cylindrical cam 341 may be moved only in one direction. In this case, the transfer member 331 and the transducer 314 can perform a forward or backward motion according to a rotational direction of the cylindrical cam 341. For example, when the cylindrical cam 341 rotates clockwise, the transfer member 331 and the transducer 314 advance and the cylindrical cam 341 rotates counterclockwise, the transfer member 331 and the transducer 314 can retreat. Meanwhile, in the ultrasonic wave generating device 10 according to an embodiment of the present disclosure, the rotational force applying unit 350 and the outer rotating unit 233 are coupled to each other due to magnetism. Thus, when the rotational direction is suddenly changed, magnetic coupling between the rotational force applying unit 350 and the outer rotating unit 233 can be instantaneously cut off. Thus, a diameter or rotational speed of the cylindrical cam 341 can be determined in consideration of the magnetic coupling force between the rotational force applying unit 350 and the outer rotating unit 233 and the rectilinear reciprocating speed of the transducer 314.

In an embodiment, a permeable member may be provided in a direction in which ultrasonic waves generated in the transducer 314 of the first cartridge 310 pass. In this case, the permeable member may be a window formed of a material through which ultrasonic waves can be smoothly transmitted.

In addition, a fluid L may be filled in an empty space of the inside of the first cartridge 310. The fluid L serves as a kind of medium through which the ultrasonic waves generated in the transducer 314 are smoothly transferred to the outside of the first cartridge 310. In addition, the fluid L may perform a function of cooling the transducer 314. For example, while the transducer 314 generates ultrasonic waves, a heating phenomenon may occur. The heating phenomenon may be alleviated using the above-described fluid F.

Thus, it is desired for the above-described fluid F to be filled in at least a region from the permeable member of the first cartridge 310 to the transducer 314. In addition, while a procedure is performed in a state in which the first cartridge 310 is coupled to the procedure handpiece and is in contact with the body of a procedural subject, the permeable member of the first cartridge 310 may not always be in a vertically downward direction. Thus, in one form, a filling amount of the above-described fluid L is determined in consideration of an inclination range of a direction of the transducer 314 during a procedure. Of course, the above-described fluid L may also be fully filled in the empty space of the inside of the first cartridge 310.

Meanwhile, when the fluid L is filled in the first cartridge 310, a loss period of the fluid L may be changed according to a sealing degree of the inside of the first cartridge 310. For example, when the sealing degree of the inside of the first cartridge 310 is low, the amount of fluid L inside the first cartridge 310 may be reduced as time elapses. In this case, a problem in that it is necessary for the fluid L to be supplemented or the first cartridge 310 itself has to be replaced may occur. However, in the ultrasonic wave generating device 10 according to an embodiment of the present disclosure, the rotational force applying unit 350 provided inside the cartridge receives the rotational force from the outer rotating unit 233 provided outside the cartridge. The applied rotational force may be converted by the above-described conversion unit so that the transducer 314 can perform a rectilinear motion or rectilinear reciprocating motion. Also, because the rotational force applying unit 350 and the outer rotating unit 233 can be connected to each other due to magnetism, the sealing degree the first cartridge 310 can be improved. That is, in the ultrasonic wave generating device 10 according to an embodiment of the present disclosure, the transducer 314 can perform a rectilinear motion or rectilinear reciprocating motion by using a driving force outside the first cartridge 310 without an element that passes through an outer wall of the first cartridge 310 or the housing 312.

Thus, in the ultrasonic wave generating device 10 according to an embodiment of the present disclosure, the sealing degree of the cartridge can be improved compared to the case in which an element passing through the outer wall of the cartridge or the housing 312 is required. Thus, a replacement period of the cartridge can be extended, and convenience of use and maintenance of the ultrasonic wave generating device can be improved. Also, it is not necessary for the ultrasonic wave generating device 10 according to an embodiment of the present disclosure to include an additional unit for improving the sealing degree of the cartridge, and the transducer 314 can perform a rectilinear motion or rectilinear reciprocating motion with a simplified structure through the above-described rotational force applying unit 350 and the conversion unit so that miniaturization of the cartridge or the procedure handpiece and a reduction in manufacturing costs can be achieved.

The first cartridge 310 has been described above. However, because the second cartridge 310-1 or the third cartridge 310-2 can be implemented in a similar manner to that of the first cartridge 310, redundant descriptions thereof will be omitted.

Figure 3:
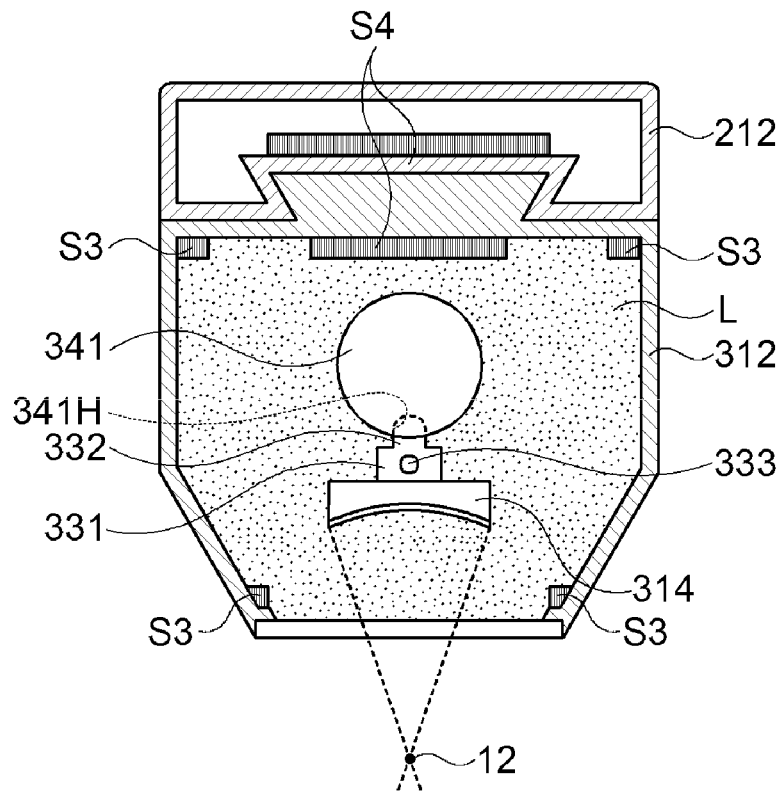
FIG. 3 is a view schematically illustrating a cut surface taken along line I-I' of FIG. 2.

In addition, reference symbols S3 and S4 indicated in FIG. 3 represent a third sensor and a fourth sensor, respectively. An embodiment in which these sensors are included will be described later with reference to FIGS. 13 to 20.

Hereinafter, an ultrasonic wave generating device according to another embodiment of the present disclosure will be described with reference to FIGS. 6 to 11. Here, the same descriptions as the above descriptions may be omitted.

Referring to FIGS. 6 to 11, an ultrasonic wave generating device 20 according to an embodiment of the present disclosure may include a procedure handpiece 410 and a cartridge set 500, and furthermore may further include a cradle 600. Here, the procedure handpiece 410 and a cartridge may be also referred to as a handpiece assembly 400.

In this case, the procedure handpiece 410 is used to radiate HIFU onto a procedural subject, and may have a hand-held shape so as to improve convenience of user manipulation. For example, the procedure handpiece 410 may have a shape by which a practitioner grips the procedure handpiece 410 comfortably.

Figure 6:
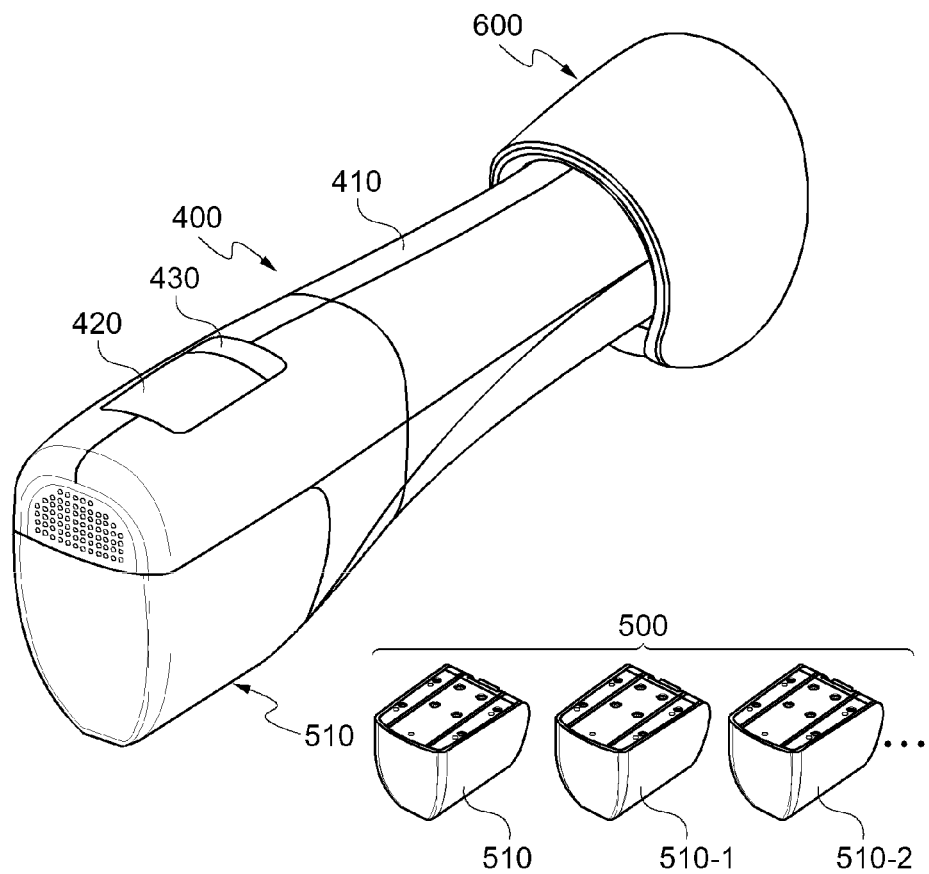
FIG. 6 is a perspective view schematically illustrating an ultrasonic wave generating device according to another embodiment of the present disclosure.

In an embodiment, the procedure handpiece 410 may include a display unit 420 for providing procedural information to a practitioner (not shown), and an input unit 430 to which a predetermined command from the practitioner is input. Here, the input unit 430 may be implemented as a physical button or touch screen manner. In FIG. 6 and the like, although the display unit 420 and the controller 440 are separately illustrated, it is obvious that the display unit 420 and the input unit 430 may be integrally formed in the touch screen manner.

Figure 9:
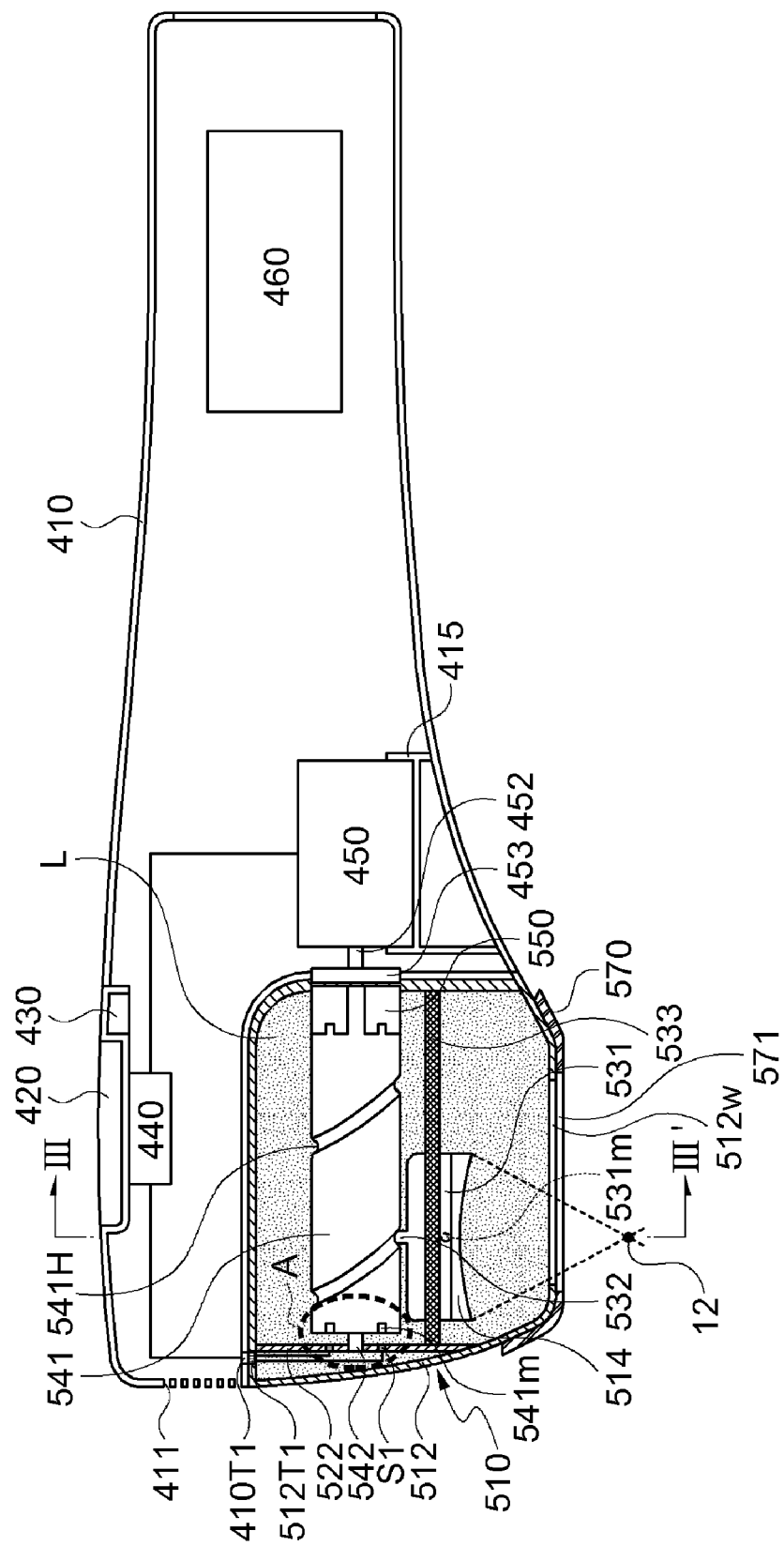
FIG. 9 is a cross-sectional view schematically illustrating an ultrasonic wave generating device according to another embodiment of the present disclosure.
Figure 10:
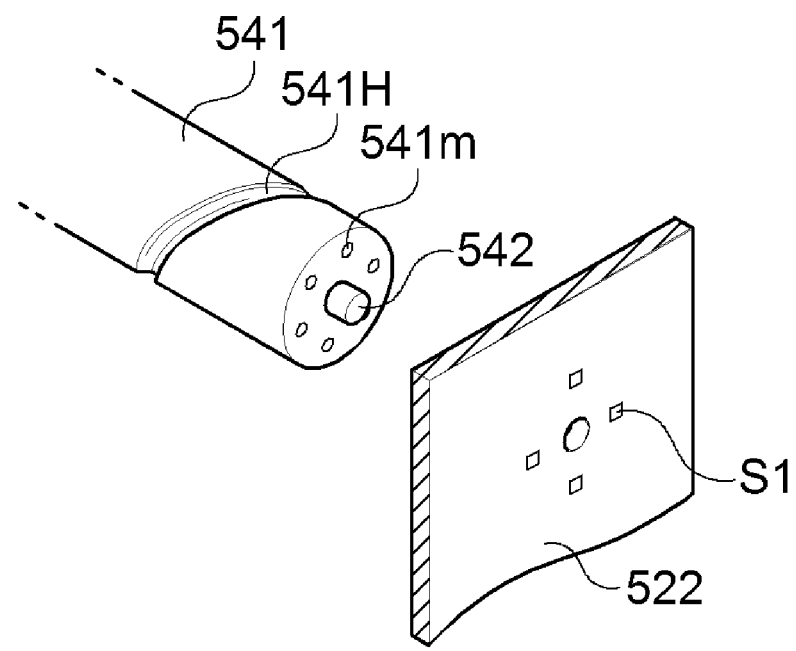
FIG. 10 is a partially-extracted perspective view schematically illustrating portion A of FIG. 9.
Figure 11:
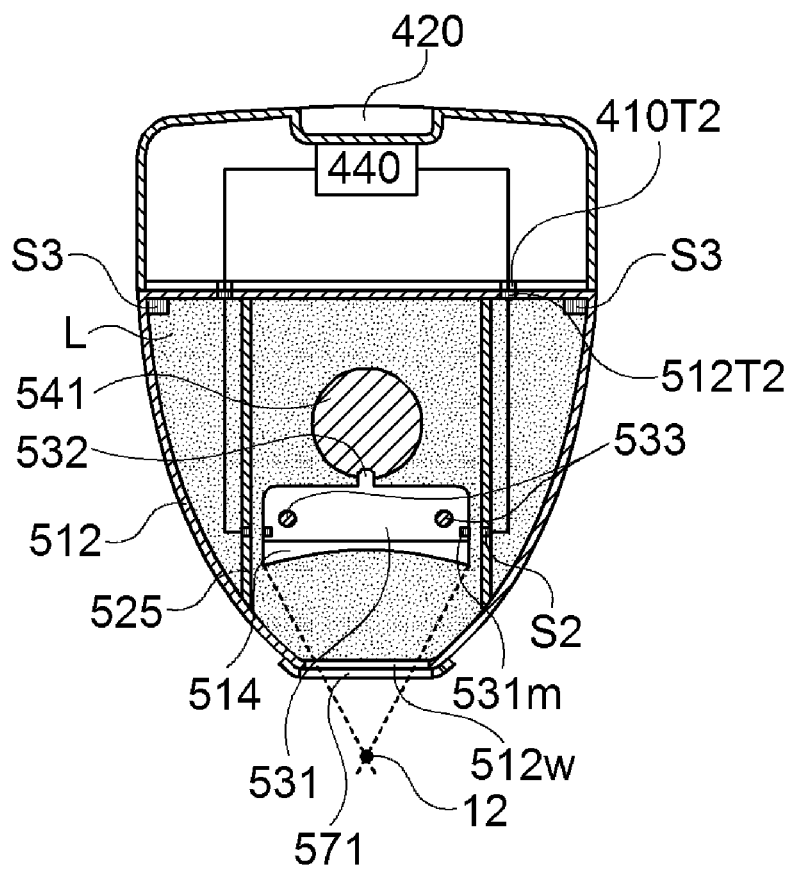
FIG. 11 is a cross-sectional view schematically illustrating a cut surface taken along line III-III' of FIG. 9.

The display unit 420 and the input unit 430 may be connected to the controller 440 illustrated in FIG. 9 and the like, and a command of the practitioner applied to the input unit 430 may be transferred to the controller 440 so that the ultrasonic wave generating device 20 can operate or can be controlled.

In an embodiment, a power supply unit 460 may be provided inside the procedure handpiece 410. In this case, it is not necessary for an additional cable for supplying external power to be connected to the procedure handpiece 410 so that convenience during various procedures using the procedure handpiece 410 can be improved. Here, the power supply unit 460 may be implemented with a secondary battery such as a lithium ion battery. Furthermore, when the procedure handpiece 410 is held on the cradle 600, the power supply unit 460 may be implemented such that the power supply unit 460 can be charged. Meanwhile, a vent 411 may perform a function of flowing air through an inside of the procedure handpiece 410 so that an overheating phenomenon of the procedure handpiece 410 and the cartridge can be alleviated.

Next, the cartridge set 500 may be a set including a plurality of cartridges. In an example, the cartridge set 500 may include first through third cartridges 510, 510-1, and 510-2 having the same or similar procedure types or procedure conditions. Each of the first through third cartridges 510, 510-1, and 510-2 may be configured to be attached to or detached from the procedure handpiece 410.

As described above, the ultrasonic wave generating device 20 according to an embodiment of the present disclosure includes the cartridge set 500 including the first through third cartridges 510, 510-1, and 510-2 having the same procedure types or procedure conditions and replaces an exhausted cartridge with a new cartridge and mounts the new cartridge on the procedure handpiece 410 so that, when a service life of the transducer 514 expires, the ultrasonic wave generating device 20 may not be newly purchased but may be continuously used by replacing the cartridges.

In another example, the cartridge set 500 may include the first through third cartridges 510, 510-1, and 510-2 having different procedure types or conditions. Each of the first through third cartridges 510, 510-1, and 510-2 may be attachable to or detachable from the procedure handpiece 410. For example, functions of the first cartridge 510, the second cartridge 510-1, and the third cartridge 510-2 are classified according to a procedural subject's skin or obesity state or a procedure part, and, in detail, conditions such as a radiation intensity and a radiation depth of HIFU may be different.

In more detail, the transducer 514 provided in the cartridge set 500 may be moved in forward and backward directions so that each of the first through third cartridges 510, 510-1 and 510-2 has a procedure region of approximately 40.0 to 100.0 mm. In this case, the transducer 514 may radiate the HIFU while being moved within the above range. Meanwhile, when a forward and backward movement range of the transducer 514 is less than approximately 40.0 mm, the procedure region is small, and a procedure time can be greatly extended. In addition, because the transducer 514 is set to radiate the HIFU to a predetermined depth and the subcutaneous layer is spread in both-side directions of the human navel, when the forward and backward movement range of the transducer 514 exceeds approximately 100.0 mm, an initial HIFU radiation path and a final HIFU radiation depth with respect to the subcutaneous layer may be different. As a result, a risk of the HIFU being radiated in a region that deviates from the subcutaneous layer can be greatly increased. Thus, the transducer 514 may be set to be moved forward and backward in the range of approximately 40.0 to 100.0 mm, or in the range of approximately 60.0 to 80.0 mm which is advantageous in securing procedure safety and a reduction in a procedure time.

Meanwhile, even in the ultrasonic wave generating device 20 according to an embodiment of the present disclosure, a rotational force outside the first through third cartridges 510, 510-1, and 510-2 may be transferred to an inside of the cartridge, and the transducer 514 may be moved in a rectilinear direction using the rotational force.

In an embodiment, the first cartridge 510 may include a rotational force applying unit 550 provided inside a region surrounded by the housing 512, a conversion unit, and the transducer 514.

The rotational force applying unit 550 performs a function of applying a rotational force provided from an outside of the housing 512. In an example, the rotational force may be transferred from an outer rotating unit 453 that performs a rotational motion from the outside of the housing 512 to the rotational force applying unit 550. Here, the rotational force applying unit 550 and the outer rotating unit 453 are not in direct contact with each other and face each other in a state in which the housing 512 is disposed therebetween. The rotational force applying unit 550 and the outer rotating unit 453 may be connected to each other due to magnetism. To this end, the rotational force applying unit 550 and the outer rotating unit 453 may be formed of a magnetic material or may include a magnetic material. In addition, a region between the rotational force applying unit 550 of the housing 512 and the outer rotating unit 453 is formed of a non-magnetic material so that a reduction in a magnetic coupling force between the rotational force applying unit 550 and the outer rotating unit 453 can be minimized. Of course, although the entire housing 512 may be formed of the non-magnetic material, when the housing 512 is not the region between the rotational force applying unit 550 and the outer rotating unit 453, the housing 512 may be formed of a magnetic material.

In an embodiment, the rotational force applying unit 550 and the outer rotating unit 453 may have a general disc shape. Thus, the magnetic coupling force between the rotational force applying unit 550 and the outer rotating unit 453 can be increased, a minimum of space is required, and a frictional force therebetween can be reduced.

In addition, a concave portion is provided in the housing 512, and a part of the rotational force applying unit 550 and the outer rotating unit 453 is inserted into the concave portion so that the rotational force applying unit 550 and the outer rotating unit 453 can be stably supported and can smoothly perform a rotational motion.

In addition, a member such as a bearing may be provided between the rotational force applying unit 550 and the housing 512 and between the outer rotating unit 453 and the housing 512 so that a frictional force therebetween can be reduced and a smooth rotational motion can be performed through the bearings.

In an embodiment, the outer rotating unit 453 may be connected to a rotating shaft 452 of a motor 450. The motor 450, the rotating shaft 452, and the outer rotating unit 453 may be provided in the procedure handpiece 410.

Figure 7:
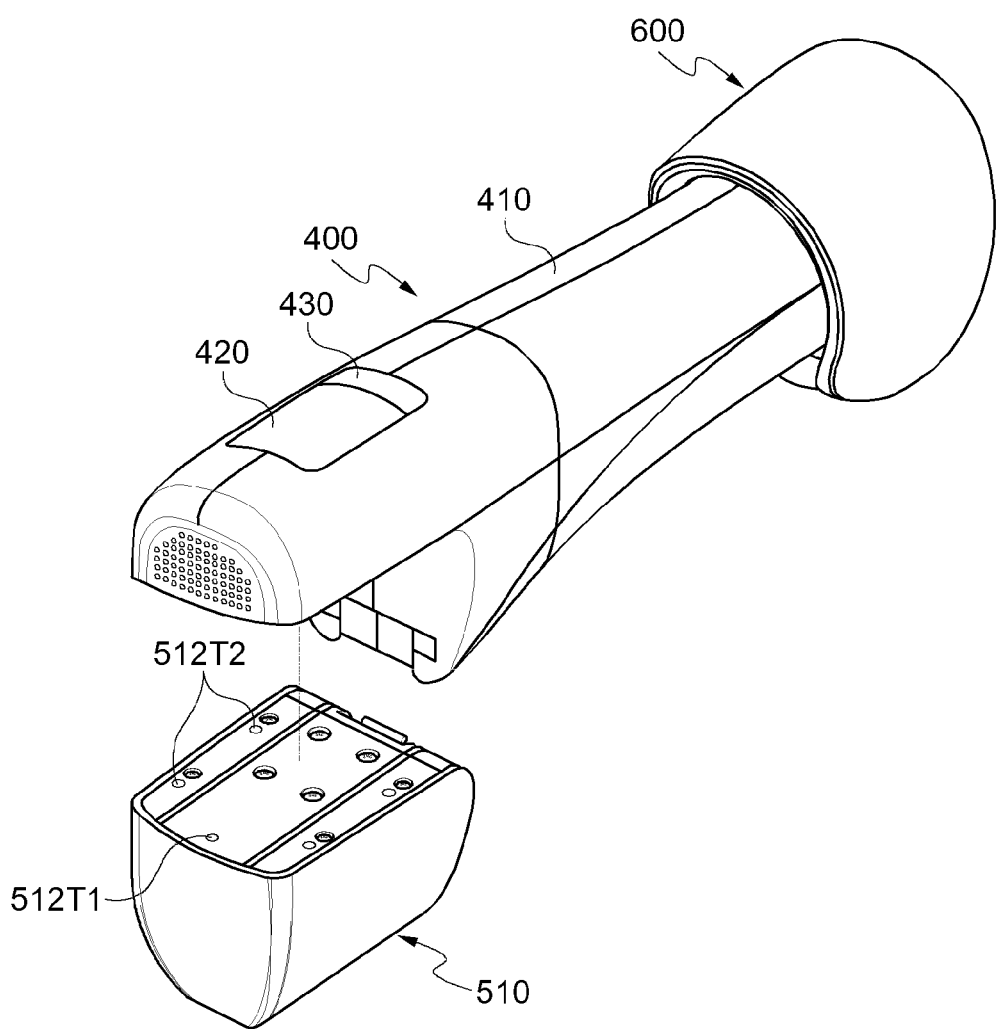
FIG. 7 is a view for explaining a combination relationship between a procedure handpiece and a cartridge illustrated in FIG. 6.
Figure 8:
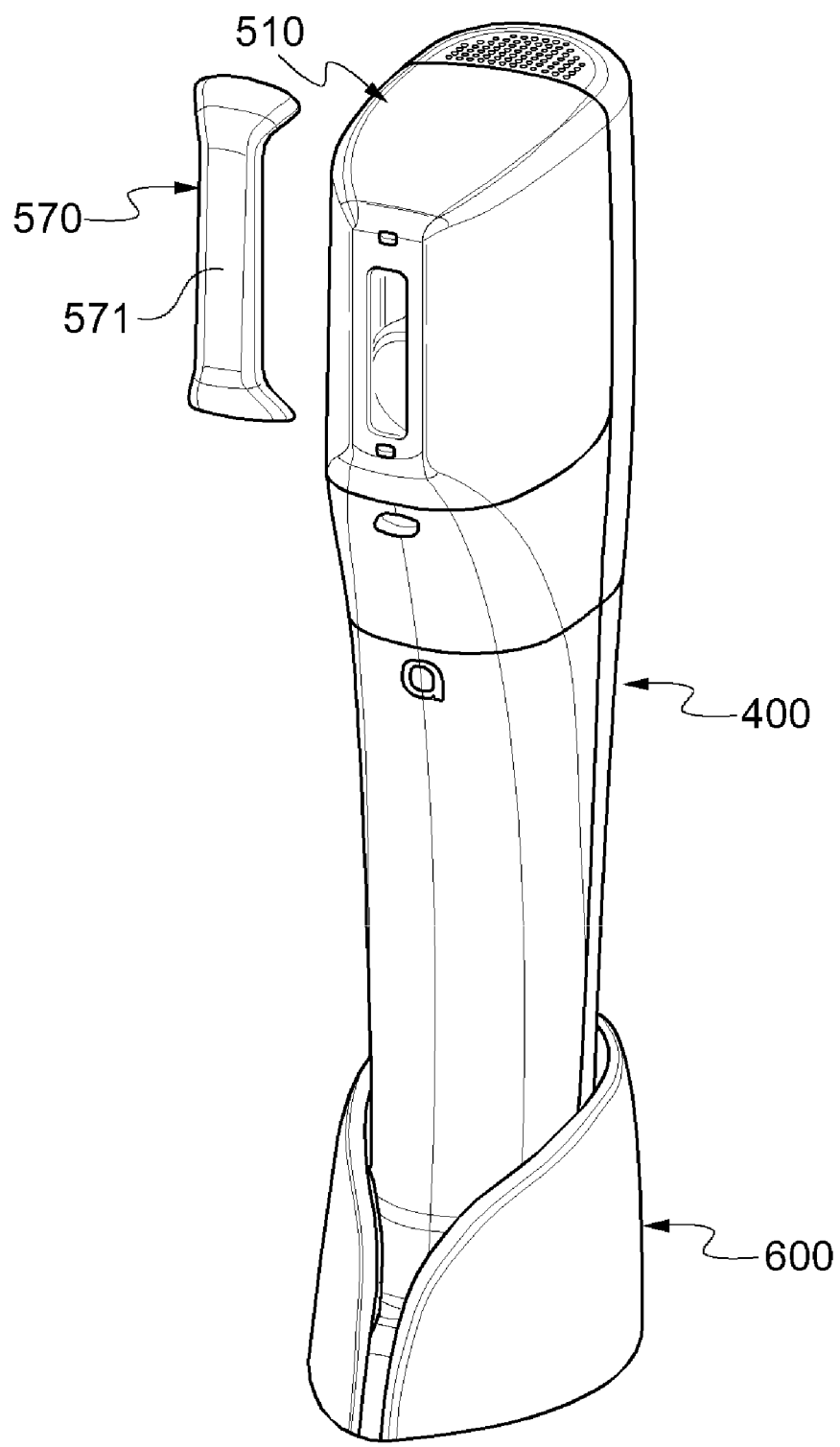
FIG. 8 is a view schematically illustrating an ultrasonic wave generating device according to another embodiment of the present disclosure.

Here, referring to FIG. 7, the first cartridge 510 may be coupled to the procedure handpiece 410. In this case, the outer rotating unit 453 is disposed at a portion at which the first cartridge 510 and the procedure handpiece 410 are in contact with each other. As illustrated in FIG. 9, at least a part of the outer rotating unit 453 protrudes toward an outside of the procedure handpiece 410 and is inserted into the concave portion of the housing 512 so that the magnetic coupling force between the outer rotating unit 453 and the rotational force applying unit 550 can be increased. Of course, although not shown, a surface of the housing 512 with which the rotational force applying unit 550 is in contact protrudes in a direction of the outer rotating unit 453, and a protruding portion thereof may be inserted into the inside of the procedure handpiece 410.

Meanwhile, the conversion unit is provided between the rotational force applying unit 550 and the transducer 514 and performs a function of converting the rotational motion of the rotational force applying unit 550 into a rectilinear motion and providing the rectilinear motion to the transducer 514. Thus, the transducer 514 may be moved in the rectilinear direction from the inside of the first cartridge 510.

In an embodiment, the conversion unit may include a driving joint that performs a rotational motion and a driven joint that performs a rectilinear motion. For example, the driving joint is constituted by forming a groove portion 541H having a spiral shape in a surface of a cylindrical cam 541 having a cylindrical shape and may perform a rotational motion, and the driven joint is constituted by moving a transfer member 531 including a protrusion 532 inserted into the groove portion 541H of the cylindrical cam 541 in the rectilinear direction along a guide portion 533. Although not shown, protrusions having a spiral shape may be formed on the surface of the cylindrical cam 541, and a concave groove into which the protrusions are inserted is provided in the transfer member 531 so that the driving joint and the driven joint can be coupled to each other.

In addition, the transducer 514 is fixed to the transfer member 531 so that the transducer 514 can be moved in the rectilinear direction with the transfer member 531 according to movement of the transfer member 531 in the rectilinear direction. Here, the transducer 514 and the transfer member 531 may also be referred to as an ultrasonic wave generating unit.

In an embodiment, one end of the cylindrical cam 541 is connected to the rotational force applying unit 550. The other end of the cylindrical cam 541 may be rotatably coupled to the housing 512. That is, as illustrated in FIG. 4, a concave groove is provided in the housing 512, a shaft protrusion 542 is provided on the other end of the cylindrical cam 541, and the shaft protrusion 542 is inserted into the concave groove so that the cylindrical cam 541 can be rotatably coupled to the housing 512. Thus, when the rotational force applying unit 550 receives the rotational force from the outer rotating unit 453 and performs a rotational motion, the cylindrical cam 541 can perform a rotational motion. In FIG. 9 and the like, the cylindrical cam 541 and the rotational force applying unit 550 are separate units and are coupled to each other. However, the cylindrical cam 541 and the rotational force applying unit 550 may also be integrally formed. However, it is desired for the rotational force applying unit 550 to be formed of a magnetic material or include a magnetic material to be magnetically connected to the outer rotating unit 453, whereas it is not necessary for the cylindrical cam 541 to be formed of a magnetic material. Thus, in terms of a reduction in manufacturing costs and improvements in manufacturing efficiency, it is advantageous for the cylindrical cam 541 and the rotational force applying unit 550 to be implemented using different materials and then coupled to each other. In this case, at least one hanging protrusion may be provided in a coupling portion of the cylindrical cam 541 and the rotational force applying unit 550 so that a rotational motion of the rotational force applying unit 550 can be effectively transferred to the cylindrical cam 541.

In an embodiment, the groove portion 541H provided on the surface of the cylindrical cam 541 starts from one side of the cylindrical cam 541, passes through to the other side of the cylindrical cam 541, and returns to the one end of the cylindrical cam 541 to form one round circle. In this case, when the cylindrical cam 541 rotates by 360 degrees, the transfer member 531 and the transducer 514 can perform a rectilinear motion, a so-called rectilinear reciprocating motion, to advance along the guide portion 533 and return to original positions thereof. In this case, the rotational speed of the cylindrical cam 541 can be controlled in consideration of a rectilinear reciprocating speed of the transducer 514, and a rotational speed of the above-described motor 450 can be controlled, or a rotational speed can be controlled by including a gear (not shown) between a rotating shaft of the motor 450 and the outer rotating unit 453.

In another embodiment, the groove portion 541H provided on the surface of the cylindrical cam 541 may be moved only in one direction. In this case, the transfer member 531 and the transducer 514 can perform a forward or backward motion according to a rotational direction of the cylindrical cam 541. For example, when the cylindrical cam 541 rotates clockwise, the transfer member 531 and the transducer 514 advance and the cylindrical cam 541 rotates counterclockwise, and the transfer member 531 and the transducer 514 can retreat. Meanwhile, in the ultrasonic wave generating device 20 according to an embodiment of the present disclosure, the rotational force applying unit 550 and the outer rotating unit 453 are coupled to each other due to magnetism. Thus, when the rotational direction is suddenly changed, magnetic coupling between the rotational force applying unit 550 and the outer rotating unit 453 can be instantaneously cut off. Thus, a diameter or rotational speed of the cylindrical cam 541 can be determined in consideration of the magnetic coupling force between the rotational force applying unit 550 and the outer rotating unit 453 and a rectilinear reciprocating speed of the transducer 314.

Meanwhile, the ultrasonic wave generating device 20 according to an embodiment of the present disclosure may include a position detection unit and a controlling means. Here, the position detection unit detects a position of an ultrasonic wave generating unit, and the controlling means controls an ultrasonic wave generating operation using the result of the detection performed by the position detection unit. For example, after ultrasonic waves are generated in a state in which the ultrasonic wave generating unit is disposed in any one position, the controlling means controls the ultrasonic wave generating operation not to generate ultrasonic waves in a state in which the ultrasonic wave generating unit is not moved a predetermined distance.

When the ultrasonic waves generated in the ultrasonic wave generating unit are HIFU, a thermal lesion is formed at a predetermined part, but there is a risk of human tissue being unintentionally damaged when the thermal lesion excessively continues at the same position. That is, when the thermal lesion is formed at the predetermined part and a thermal lesion is formed again in a state in which the ultrasonic wave generating unit is not moved the predetermined distance, a predetermined point of human tissue is excessively stimulated so that pain, bleeding, or injury may occur. However, according to an embodiment of the present disclosure, when the ultrasonic wave generating unit is not moved the predetermined distance or more immediately after ultrasonic waves are generated in the ultrasonic wave generating unit, the ultrasonic wave generating device 20 can operate not to generate ultrasonic waves so that the above-described risk can be remarkably reduced. Here, whether the ultrasonic wave generating unit is moved may be detected by the above-described position detection unit, and the controlling means controls whether ultrasonic waves are generated by the ultrasonic wave generating unit on the basis of the detection result so that the risk of the ultrasonic waves being excessively radiated onto a predetermined position can be reduced. Meanwhile, the above-described 'predetermined distance' may be properly determined according to a strength of the ultrasonic waves generated in the ultrasonic wave generating unit, a size of the thermal lesion, and the type of tissue onto which ultrasonic wave is radiated.

In addition, because the ultrasonic wave generating unit, which is a concept including the above-described transducer 514 and transducer 531, performs a rectilinear motion in a state in which the transducer 514 is coupled to the transfer member 531, the position detection unit detects a position of the transducer 514 or a transfer unit so that the ultrasonic wave generating unit can perform a function thereof. In addition, the transfer unit performs a rectilinear motion according to a rotation of the above-described cylindrical cam 541 to detect a degree of rotation of the cylindrical cam 541 and thus detect the position of the ultrasonic wave generating unit.

In an embodiment, the position detection unit may include a magnet unit and a sensor, and here the sensor may be a hall sensor. A signal output from the sensor is changed according to a positional relationship between the magnet unit and the hall sensor, and a relative positional relationship between the magnet unit and the sensor can be detected using a degree of change.

In more detail, the ultrasonic wave generating device 20 according to an embodiment of the present disclosure may include a first magnet unit 541*m* provided in the cylindrical cam 541 and a first sensor S1 that faces the first magnet unit 541*m*. In this case, because the rotational force applying unit 550 having magnetism is provided at the one end of the cylindrical cam 541, the first magnet unit 541*m* is provided at the other end of the cylindrical cam 541. Thus, the first sensor S1 may more precisely detect a position or movement of the first magnet unit 541*m*. Meanwhile, although the first magnet unit 541*m* is provided in the cylindrical cam 541 in the drawings, the first sensor may also be provided in the cylindrical cam 541 according to circumstances. However, in comparison to the case in which the first sensor is provided in the cylindrical cam 541 that performs a rotational motion, when a signal output from the first sensor is transmitted to the controller 440, the first sensor S1 is provided in a fixed structure such as the housing 512 or the first frame 522 so that simplification of a structure and improvements in manufacturing efficiency can be achieved.

Thus, a degree of rotation of the cylindrical cam 541 can be precisely measured, and as a result thereof the position of the ultrasonic wave generating unit can be determined.

The ultrasonic wave generating device 20 according to another embodiment of the present disclosure may include a second magnet unit 531*m* provided in the ultrasonic wave generating unit and a second sensor S2 that faces the second magnet unit 531*m*. Here, although the second magnet unit 531*m* is provided in the transfer member 531 in FIG. 9 and the like, the second magnet unit 531*m* may also be provided in the transducer 514. In addition, although the second magnet unit 531*m* is provided in the transfer member 531 in the drawings, the second sensor may also be provided in the transfer member 531 according to circumstances. However, in comparison to the case in which the first sensor is provided in the transfer member 531 that performs a rectilinear motion, when a signal output from the second sensor is transmitted to the controller 440, the second sensor S2 is provided in a fixed structure such as the housing 512 or the second frame 525 so that simplification of a structure and improvements in manufacturing efficiency can be achieved.

Meanwhile, the second sensor S2 may be provided to face the second magnet unit 531*m*. As described above, the transfer member 531 and the transducer 514 perform a rectilinear reciprocating motion inside the first cartridge 510 to limit movement range thereof. That is, the transfer member 531 can perform a rectilinear reciprocating motion only in a region between a position at which the transfer member 531 is spaced farthest apart from the rotational force applying unit 550 and a position at which the transfer member 531 is disposed closest to the rotational force applying unit 550. Here, the position at which the transfer member 531 is spaced farthest apart from the rotational force applying unit 550 may be referred to as a first reference point, and the position at which the transfer member 531 is disposed closest to the rotational force applying unit 550 may be referred to as a second reference point. In this case, when the transfer member 531 is disposed at the first reference point, the second sensor S2 may be provided closest to the second magnet unit 531*m*. Also, when the transfer member 531 is disposed at the second reference point, the second sensor S2 may be provided closest to the second magnet unit 531*m*. Thus, the position detection unit can precisely detect the position of the ultrasonic wave generating unit at a turning point in which a movement direction of the ultrasonic wave generating unit is changed. Also, the instant that a rectilinear motion of the ultrasonic wave generating unit starts and ends one cycle can be precisely detected. That is, an initial position of the ultrasonic wave generating unit and a movement end position of the ultrasonic wave generating unit can be precisely detected.

In a system in which a rotational force is transferred in a state in which the rotational force applying unit 550 and the outer rotating unit 453 are not directly coupled to each other but are connected to each other due to magnetism, a rotational motion of the outer rotating unit 453 and a rotational motion of the rotational force applying unit 550 may not completely coincide with each other. As a result, the position of the ultrasonic wave generating unit cannot be precisely measured or a degree of movement of the ultrasonic wave generating unit cannot be completely controlled only by controlling or measuring a degree of rotation of the outer rotating unit 453. Thus, when there is no additional unit for precisely checking the position of the ultrasonic wave generating unit, there is a risk of ultrasonic waves being excessively radiated onto a predetermined position as described above which results in the occurrence of several problems.

However, since the ultrasonic wave generating device 20 according to an embodiment of the present disclosure includes the above-described position detection unit and controlling means, the above-described risk can be remarkably reduced by precisely checking the position of the ultrasonic wave generating unit and reflecting the found position of the ultrasonic wave generating unit on control of the ultrasonic wave generating operation.

Meanwhile, an additional frame is provided inside the housing 512 so that the first sensor S1 or the second sensor S2 can be fixed at a proper position. For example, the first sensor S1 may be fixed to the first frame 522 provided in front of the cylindrical cam 541, and the second sensor S2 may be fixed to the second frame 525 provided at a side of the cylindrical cam 541. Here, the shaft protrusion 542 of the cylindrical cam 541 is also inserted into the first frame 522 and may be rotatably fixed thereto. Also, a plurality of first sensors S1 and a plurality of first magnet units 541m may be provided so that rotation of the cylindrical cam 541 can be more precisely detected. A first terminal 512T1 connected to the first sensor S1 and a second terminal 512T2 connected to the second sensor S2 are exposed to the outside of the housing 512 to be in contact with a first contact point 410T1 and a second contact point 410T2 provided in the procedure handpiece 410, respectively, so that the signals output from the first sensor S1 and the second sensor S2 can be transmitted to the controller 440. Here, the controller 440 may be connected to the motor 450 to control rotation of the motor 450, and the motor 450 may be fixed to the inside of the procedure handpiece 410 through a third frame 415.

In an embodiment, a permeable member may be provided in a direction through which the ultrasonic waves generated in the transducer 514 of the first cartridge 510 pass. In this case, the permeable member may be a first window 512w formed of a material through which ultrasonic wave may be smoothly transmitted.

In another embodiment, a protective cap 570 may be provided to be coupled to an outside of the first cartridge 510. Here, a second window 571 formed of a material through which ultrasonic wave may be smoothly transmitted may be provided in a direction of the protective cap 570 through which ultrasonic waves pass.

The protective cap 570 may perform a function of preventing damage or contamination of the above-described first window 512w. That is, when the first window 512w is damaged, the first cartridge 510 has to be repaired or discarded. However, when the second window 571 of the protective cap 570 is damaged, the first cartridge 510 can be continuously used by replacing only the protective cap 570 so that a service life of the cartridge can be extended.

Also, a radiation depth of the ultrasonic waves can also be adjusted by changing a thickness of the protective cap 570. That is, in the case in which a thick protective cap 570 is used, a depth of a thermal lesion may be close to a surface of the skin when compared to the case in which a thin protective cap 570 is used.

In addition, a fluid L may be filled in an empty space of the inside of the first cartridge 510. The fluid L serves as a kind of medium through which the ultrasonic waves generated in the transducer 514 are smoothly transferred to an outside of the first cartridge 510. In addition, the fluid L may perform a function of cooling the transducer 514. For example, while the transducer 514 generates ultrasonic waves, a heating phenomenon may occur, and the heating phenomenon may be alleviated using the above-described fluid F.

Thus, it is necessary for the above-described fluid F to be filled in at least a region from the permeable member of the first cartridge 510 to the transducer 514. In addition, while a procedure is performed in a state in which the first cartridge 510 is coupled to the procedure handpiece 410 and is in contact with the body of a procedural subject, the permeable member of the first cartridge 510 may not always be in the vertically downward direction. Thus, a filling amount of the above-described fluid L may be determined in consideration of an inclination range of a direction of the transducer 514 during a procedure. Of course, the above-described fluid L may also be fully filled in the empty space of the inside of the first cartridge 510.

Meanwhile, when the fluid L is filled in the first cartridge 510, a loss period of the fluid L may be changed according to a sealing degree of the inside of the first cartridge 510. For example, when the sealing degree of the inside of the first cartridge 510 is low, the amount of the fluid L inside the first cartridge 310 may be reduced as time elapses. In this case, a problem in that it is necessary for the fluid L to be supplemented or the first cartridge 510 itself to be replaced may occur. However, in the ultrasonic wave generating device 20 according to an embodiment of the present disclosure, the rotational force applying unit 550 provided inside the cartridge receives the rotational force from the outer rotating unit 453 provided outside the cartridge. The applied rotational force may be converted by the above-described conversion unit so that the transducer 514 can perform a rectilinear motion or rectilinear reciprocating motion. Also, because the rotational force applying unit 550 and the outer rotating unit 453 can be connected to each other due to magnetism, the sealing degree of the first cartridge 510 can be improved. That is, in the ultrasonic wave generating device 20 according to an embodiment of the present disclosure, the transducer 514 can perform a rectilinear motion or rectilinear reciprocating motion by using a driving force outside the first cartridge 510 without an element that passes through an outer wall of the first cartridge 510 or the housing 512.

Thus, in the ultrasonic wave generating device 20 according to an embodiment of the present disclosure, the sealing degree of the cartridge can be improved compared to the case in which an element passing through the outer wall of the cartridge or the housing 512 is required. Thus, a replacement period of the cartridge can be extended, and convenience of use and maintenance of the ultrasonic wave generating device 20 can be improved. Also, it is not required for the ultrasonic wave generating device 20 according to an embodiment of the present disclosure to include an additional unit for improving the sealing degree of the cartridge, and the transducer 514 can perform a rectilinear motion or rectilinear reciprocating motion with a simplified structure through the above-described rotational force applying unit 350 and the conversion unit so that miniaturization of the cartridge or the procedure handpiece 410 and a reduction in manufacturing costs can be achieved.

The first cartridge 510 has been described above. However, because the second cartridge 510-1 or the third cartridge 510-2 can be implemented in a similar manner to that of the first cartridge 510, redundant descriptions thereof will be omitted.

In addition, the reference symbol S3 indicated in FIG. 6 represents a third sensor. An embodiment in which a third sensor and the like are included will be described later with reference to FIGS. 13 to 20.

Hereinafter, an ultrasonic wave generating device according to another embodiment of the present disclosure will be described with reference to FIGS. 12 to 20. Here, the descriptions as the above descriptions may be omitted.

Figure 12:
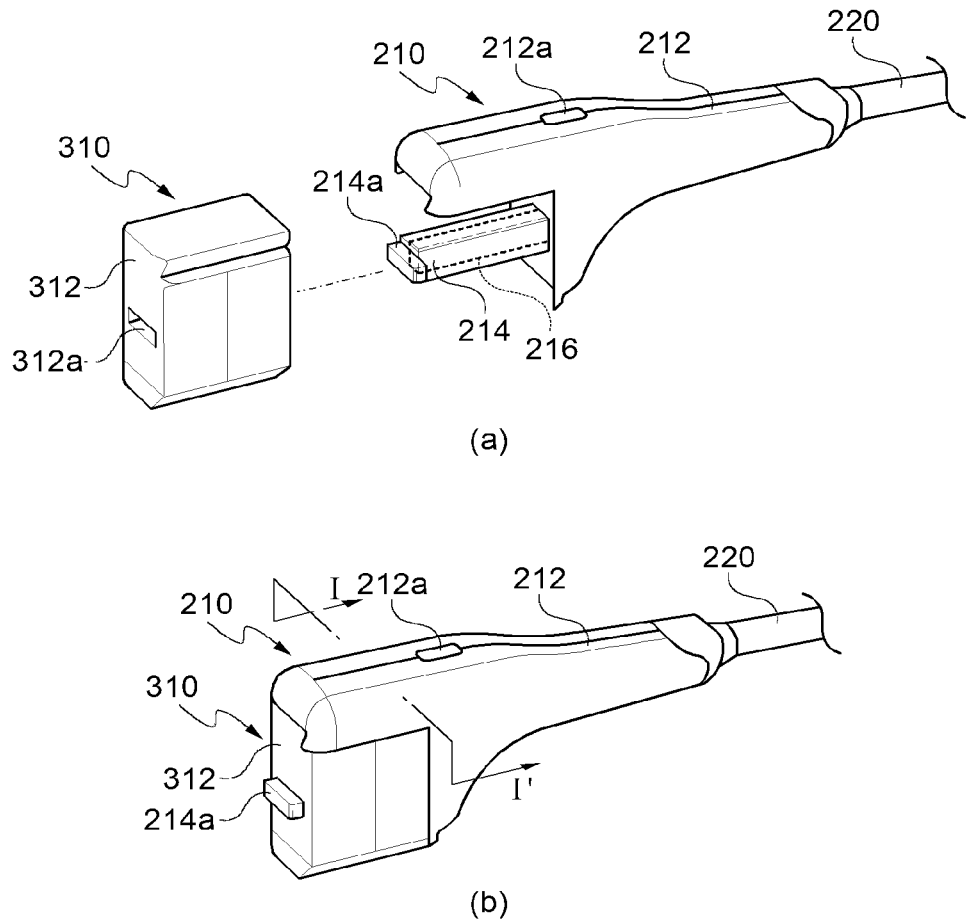
FIG. 12 is a view for explaining an operation of coupling a procedure handpiece to a cartridge.
Figure 13:
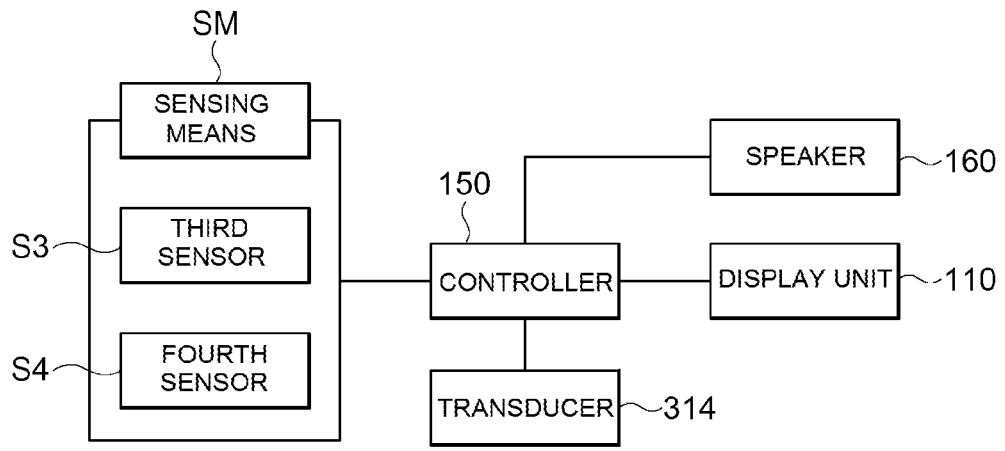
FIG. 13 is a block diagram schematically illustrating an ultrasonic wave generating device according to another embodiment of the present disclosure.

As described above, each of the cartridges may be configured to be attached to or detached from the procedure handpiece 210. For example, a guide portion 214 may be provided at a front end of the handle unit 212 to be fastened to the first cartridge 310. In an embodiment, the guide portion 214 may be provided to have a shape of a bar that protrudes in a front end direction of the handle unit 212. A through hole 312a having a shape corresponding to a cross-sectional shape of the guide portion 214 may be provided in a central region of a cartridge body 312 of the first cartridge 310. Thus, as illustrated in FIG. 12, the guide portion 214 is inserted into the through hole 312a so that the first cartridge 310 can be mounted on the procedure handpiece 210. In this case, a locking unit 214a may be provided at a front end of the guide portion 214 to prevent a mounting state of the first cartridge 310 from being released, and a practitioner rotates the locking unit 214a so that the first cartridge 310 can be locked or unlocked.

An image probe 216 for imaging a tissue which is a procedural subject may be provided inside the guide portion 214. The image probe 216 may be provided to have a shape of a general bar along the guide portion 214. The image probe 216 may generate video ultrasonic waves to image a skin tissue which is a procedural subject, i.e., a subcutaneous layer. The guide portion 214 may be provided to be located at an upper portion of the transducer 314 provided in the first cartridge 310 when the first cartridge 310 is fastened to the procedure handpiece 210. Thus, the transducer 314 radiates HIFU while performing a forward and backward motion at a lower portion of the guide portion 214, and the image probe 216 may be commonly used in cartridges, may generate additional video ultrasonic waves, may image the subcutaneous layer, and may display the imaged subcutaneous layer on the display unit 114.

Here, a driving device 218 may be provided in the procedure handpiece 210 to move the transducer 314 forward and backward. In an embodiment, a stepping motor and a rotating motor, and a gear, a belt, and a pulley which are operated by those motors, may be selectively used as the driving device 218, and the driving device 218 and the transducer 314 may be connected to each other using a support 316. Thus, as the driving device 218 allows the support 316 to perform a forward and backward motion, a tilting motion, and a vertical motion, the transducer 314 can perform the forward and backward motion, the tilting motion, and the vertical motion. In this way, the driving device 218 is provided to be commonly used by the cartridges and allows the transducer module 314 of each of the cartridges to perform a forward and backward motion.

The driving device 218 may be moved in the forward and backward direction to have a procedure period of approximately 40.0 to 100.0 mm. In more detail, the driving device 218 may be provided as a stepping motor and may allow the transducer 314 to perform a forward and backward motion by a length selected in the range of approximately 40.0 to 100.0 mm. In this case, the transducer 314 may radiate HIFU while being moved within the range. The transducer 314 may be set to radiate HIFU at predetermined intervals so that the thermal lesion 20 forms as a plurality of dots along the same line, or may be set to radiate HIFU so that the thermal lesion 20 forms as a straight line without intervals.

When the forward and backward movement range of the transducer 314 is less than approximately 40.0 mm, a procedure region of skin lifting, skin tightening, or the subcutaneous layer is small, and thus a procedure time can be greatly extended. In addition, because the transducer module 314 is set to radiate HIFU to a predetermined depth and the subcutaneous layer is spread to be curved in both-side directions of the human navel, when the forward and backward movement range of the transducer 314 exceeds approximately 100.0 mm, an initial HIFU radiation depth and a final HIFU radiation depth with respect to the subcutaneous layer are changed so that a risk of the HIFU being radiated in a region that deviates from the subcutaneous layer can be greatly increased. This risk may occur similarly in terms of skin lifting or skin tightening. Thus, the driving device 218 is set so that the transducer 314 can be moved in the range of approximately 40.0 to 100.0 mm, or in the range of approximately 60.0 to 80.0 mm, so that procedure safety can be secured and a procedure time can be reduced. However, when the transducer 314 is used for a cancer or tumor treatment, the forward and backward movement range of the transducer 314 may be changed according to a size or shape of cancer or tumor treatment. That is, when a size of a caner or tumor is less than approximately 40.0 mm, the forward and backward movement range of the transducer 314 is adjusted to be less than approximately 40.0 mm.

Meanwhile, a cooling fluid for cooling heat generated due to an operation of the transducer 314 may be provided in the first cartridge 310. In an embodiment, the first cartridge 310 may be provided so that coolant can be filled in the first cartridge 310, and the coolant is circulated by an additional coolant circulation line (not shown) so that an overheating phenomenon of the transducer 314 can be prevented from occurring. To this end, when the first cartridge 310 is mounted on the procedure handpiece 210, the coolant in the first cartridge 310 is connected to the coolant circulation line, and the coolant circulation line is connected to a coolant storage container (not shown) inside the equipment body 100 to circulate the coolant inside the coolant storage container. Meanwhile, although not shown, a circulation unit such as a pump may be installed on the coolant circulation line.

In the ultrasonic wave generating device 10 having the above structure, the cartridges having conditions suitable for different types of procedures can be selectively mounted on the procedure handpiece 210 so that the practitioner can select a cartridge on which a desired procedure can be performed and can mount the selected cartridge on the procedure handpiece 210 to perform the procedure. In this case, in comparison to a HIFU medical device that is capable of performing only a procedure with a single purpose, a structure of a multi-purpose ultrasonic wave medical device can be implemented because various procedures can be performed only by replacing a cartridge using one piece of equipment.

In particular, because depth and intensity conditions of HIFU and a skin tissue of an object to be imaged are very different in a case of a noninvasive ultrasonic wave procedure for face lifting, a noninvasive ultrasonic wave procedure for a reduction in a subcutaneous layer, and a cancer or tumor removal procedure, it is very difficult to implement at least two or more procedures among these procedures using one piece of equipment. However, in the ultrasonic wave generating device 10 according to an embodiment of the present disclosure, this technical barrier can be removed by providing the driving device 218 or the image probe 216 commonly used in cartridges with different procedure purposes in the procedure handpiece 210 so that different procedures can be performed by replacing the cartridge.

As described above, the ultrasonic wave generating device 10 according to an embodiment of the preset disclosure includes the cartridge set 300 including cartridges having different procedure purposes, and then selects a cartridge on which a desired procedure can be performed, and mounts the selected cartridge on the procedure handpiece 210 so that the desired procedure can be performed according to a procedure purpose. Thus, an ultrasonic wave generating device according to the present disclosure includes cartridges having various procedure purposes compatibly provided in a procedure handpiece, and then mounts a cartridge having a desired procedure purpose among face lifting or skin tightening, a reduction or removal procedure of a subcutaneous layer, and a tumor or cancer removal procedure to perform a procedure so that two or more HIFU procedures can be performed using a single piece of equipment.

Subsequently, an embodiment including a sensing means SM will be described with reference to FIGS. 13 to 20.

Referring to the drawings, an ultrasonic wave generating device 10 according to an embodiment of the present disclosure includes the sensing means SM. Furthermore, the ultrasonic wave generating device 10 may further include a controller 150 and a speaker 160.

In an embodiment, the sensing means SM performs a function of sensing the amount of a fluid L and/or an inclination of a cartridge. The ultrasonic wave generating device 10 according to an embodiment of the present disclosure may output a warning signal using a result sensed in the sensing means SM or may stop an operation of the transducer 314.

In detail, the sensing means SM may include third sensors S3 that sense the amount of the fluid L. In addition, the sensing means SM may include a fourth sensor S4 that senses at least one of an inclination, an acceleration, and an angular velocity.

In addition, the ultrasonic wave generating device 10 according to an embodiment of the present disclosure may include the controller 150 that determines whether the fluid L is insufficient or the inclination of the cartridge deviates from a normal range using the sensed result of the sensing means SM. In addition, when an abnormal state occurs, the ultrasonic wave generating device 10 according to an embodiment of the present disclosure may further include an output unit for outputting a warning signal to cause a user such as a practitioner to recognize the abnormal state. In this case, the output unit may output a visual warning signal or an auditory warning signal, and the visual warning signal may be output through the above-described display unit 110, while a speaker 160 may be used to output the auditory warning signal.

In addition, in the ultrasonic wave generating device 10 according to an embodiment of the present disclosure, when the inclination of the cartridge deviates from the normal range, an operation of the transducer 314 is stopped to cut off ultrasonic wave generation so that safety can be improved.

In an embodiment, third sensor S3 may be sensors for sensing whether each of the third sensors S3 is in contact with the fluid L. That is, the case in which each of the third sensors S3 is submerged in the fluid L is referred to as a normal state, and the case in which each of the third sensors S3 is exposed outside the fluid L is the abnormal state, and each of the third sensors S3 may output a signal value that is different from a signal value output during the normal state in the abnormal state. For example, in the normal state each of the third sensors S does not output a signal or outputs a low value, and each of the third sensors S can output a predetermined signal value such as a high signal in an emergency state.

Meanwhile, the fluid L may be the above-described cooling fluid. That is, the fluid L may perform a function of preventing the transducer 314 or adjacent element from being overheated due to heat generated during an ultrasonic wave generating operation. In addition, the fluid L may serve as a medium through which ultrasonic waves generated in the transducer 314 can be smoothly transferred to the outside of the first cartridge 310.

In an embodiment, a permeable member 318 may be provided in a direction in which the ultrasonic waves generated in the transducer 314 of the first cartridge 310 pass. In this case, the permeable member 318 may be a window formed of a material such as a film through which ultrasonic waves can be smoothly transmitted.

Thus, it is required for the above-described fluid L to be filled in at least a region from the permeable member 318 to the transducer 314 of the first cartridge 310. Also, while a procedure is being performed in a state in which the first cartridge 310 is coupled to the procedure handpiece 210 and is in contact with the body of a subject, the permeable member 318 of the first cartridge 310 may not always be in the vertically downward direction. Thus, in one form, the filled amount of the above-described fluid L is determined in consideration of a range of inclination of a direction of the transducer 314 during a procedure. Of course, the above-described fluid L may also be fully filled in the empty space of the first cartridge 310.

Hereinafter, the case in which the fluid L is fully filled in the empty space of the first cartridge 310 will be described. However, even when the fluid L is set not to be fully filled in the empty space of the first cartridge 310 as described above, a reference water level of the fluid L may be set inside the first cartridge 310. It should be understood that the reference water level may correspond to an inner upper surface of the first cartridge 310 or an inner lower surface of the first cartridge 310, which will be described later.

Meanwhile, when the sealing degree of the first cartridge 310 is low, the fluid L filled in the first cartridge 310 may be reduced. In addition, when the fluid performs the above-described cooling function, the amount of the fluid L may be reduced by naturally evaporation or evaporation during a cooling operation. However, when a reduction in the fluid L continues and the amount of the fluid L is reduced to be less than a predetermined required reference amount, a problem in which transmissibility of ultrasonic waves is reduced or the transducer 314 is overheated may occur.

Figure 14:
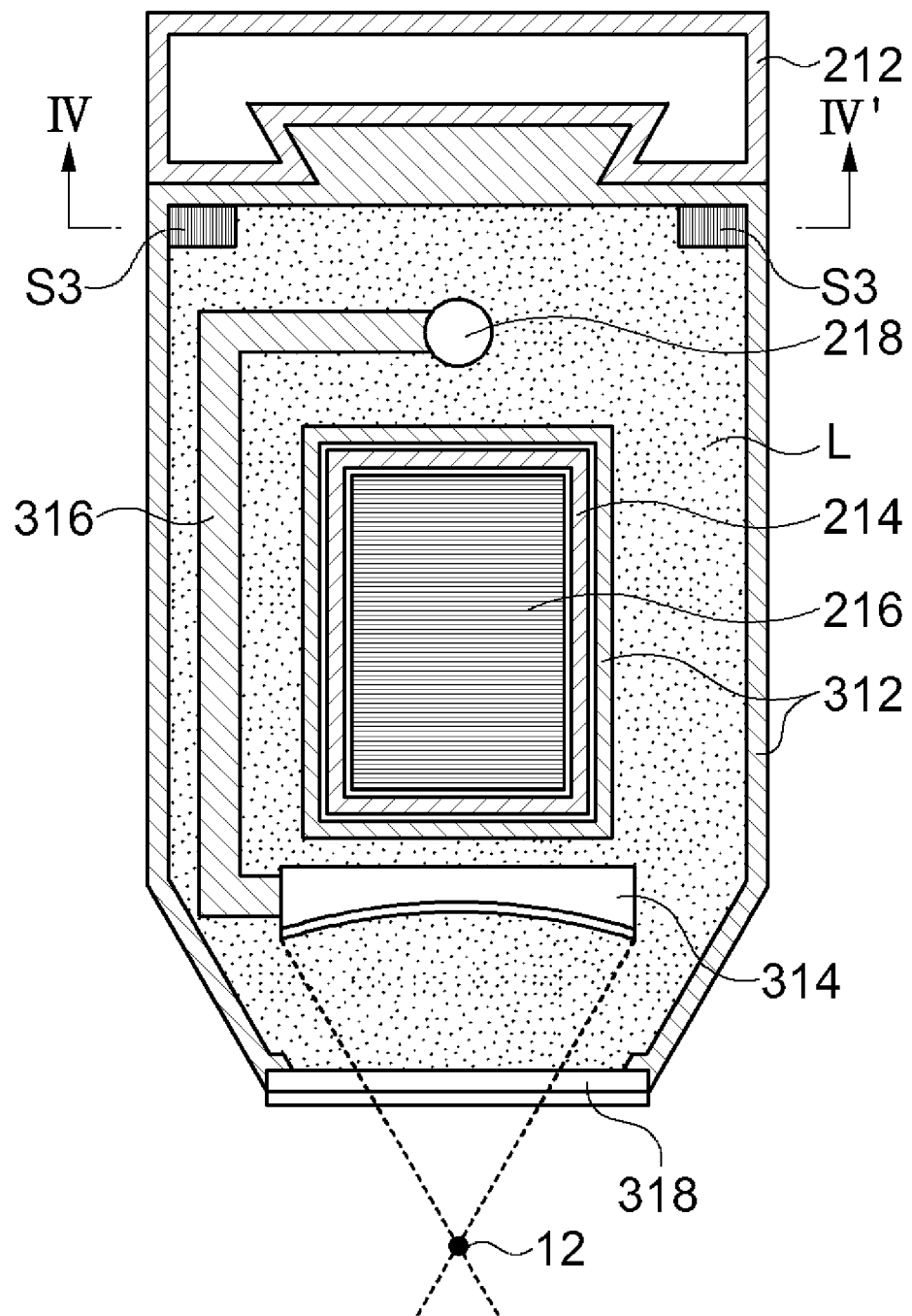
FIG. 14 is a cross-sectional view of a cut surface taken along line I-I' of FIG. 12.

In order to prevent such a problem, the above-described ultrasonic wave generating device 10 according to an embodiment of the present disclosure senses the amount of the fluid L filled in the first cartridge 310 using the above-described third sensor S3. For example, when each of the third sensors S3 is disposed at the inner upper surface of the first cartridge 310 as illustrated in FIG. 14, when the abnormal state in which the amount of the fluid L is reduced and each of the third sensors S3 is not submerged in the fluid L happens, a predetermined signal value, such as an H signal, may be transmitted to the controller 150. The controller 150 may determine the abnormal state according to the signal value provided from each of the third sensors S3 and may output a situation in which the amount of the fluid L is insufficient through the display unit 110 or may output a warning sound through the speaker 160. Thus, a user who uses the ultrasonic wave generating device 10 according to an embodiment of the present disclosure, such as a practitioner, may rapidly recognize a state in which the fluid L inside the first cartridge 310 is insufficient, and may take a proper action, such filling the fluid L or replacing the cartridge.

Figure 15:
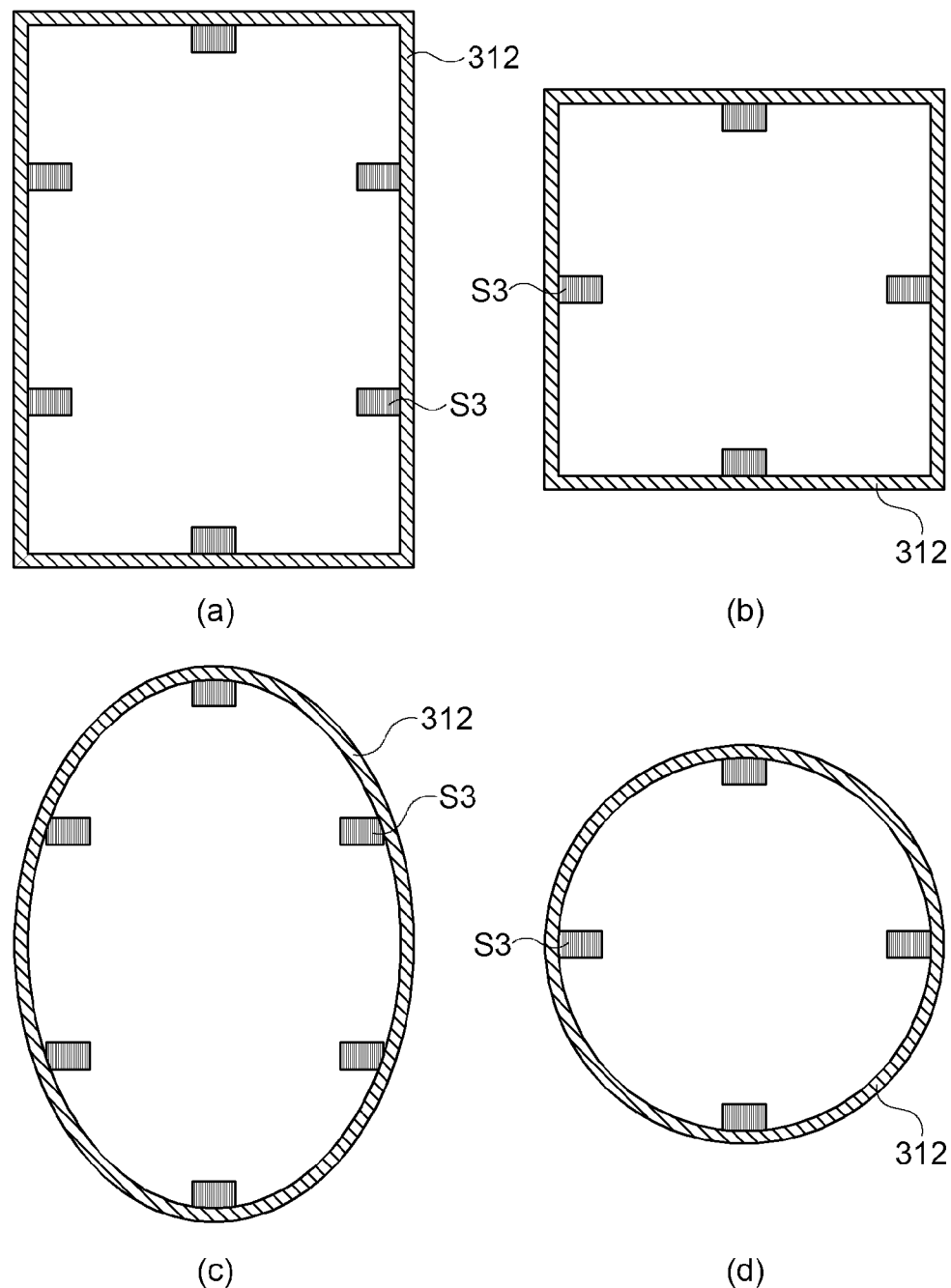
FIG. 15 is a view illustrating various modified examples of a cut surface taken along line IV-IV' of FIG. 14.

Meanwhile, in an embodiment, the plurality of third sensors S3 may be spaced apart from each other and disposed at the inner upper surface of the first cartridge 310. Referring to FIG. 15, a cross-section taken along line IV-IV' of the first cartridge 310 may have various shapes, and the third sensors S3 may be disposed in various positions according to a shape of the first cartridge 310.

Figure 16:
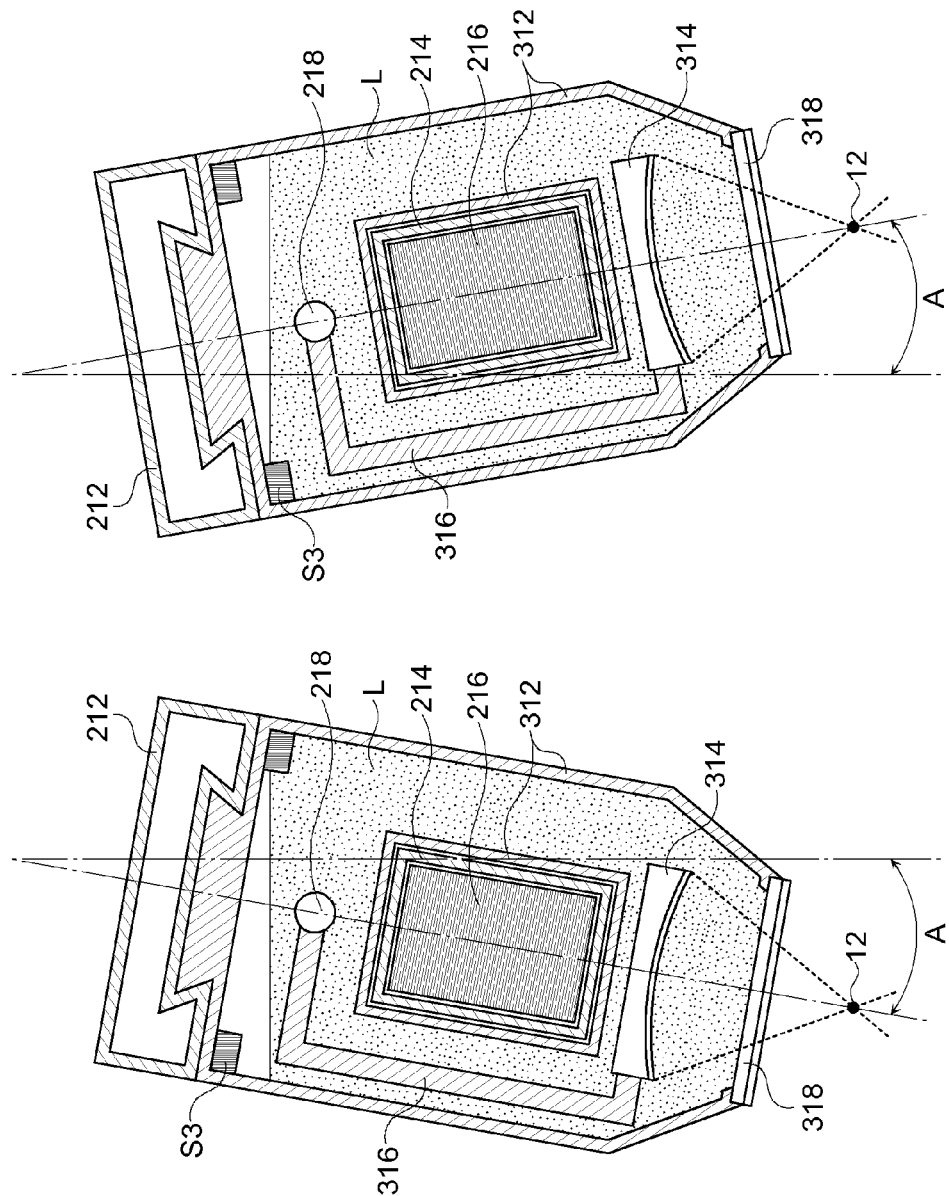
FIG. 16 is a view for explaining an operating principle of an ultrasonic wave generating device according to another embodiment of the present disclosure.

In addition, referring to FIG. 16, as the first cartridge 310 is inclined, some of the third sensors S3 may output an abnormal signal, and the remaining third sensors S3 may output a normal signal. In this way, the third sensors S3 are disposed on the inner upper surface of the first cartridge 310 and are spaced a predetermined interval apart from each other so that an inclination of the first cartridge 310 can be detected without an additional tilt sensor.

In another embodiment, the sensing means SM may detect whether a water surface (or a top surface) of the fluid L and a virtual straight line connecting the center of the permeable member 318 and the center of the transducer 314 are vertical (or horizontal) with respect to each other. That is, the sensing means SM may sense an inclination or flatness of the water surface of the fluid L. In this case, the third sensors S3 may be implemented with optical sensors. For example, the sensing means SM may include the third sensor S3 having an emission unit provided in one of the plurality of third sensors S3 and the third sensor S3 having a light-receiving unit provided in another third sensor S3. Here, light output from the third sensors S3 may have various wavelengths, such as infrared rays. The third sensor S3 having an emission unit and the third sensor S3 having a light-receiving unit may be spaced apart from each other and may face each other. Thus, in a state in which only one of the third sensor S3 having an emission unit and the third sensor S3 having the light-receiving unit is submerged in the fluid L and the other one is exposed outside the fluid L, light is refracted on the water surface of the fluid L (a boundary surface between the fluid and gas) so that a light emitted from the emission unit does not reach the light-receiving unit. On the other hand, in a state in which all of the third sensor S3 having the emission unit and the third sensor S3 having the light-receiving unit are exposed outside the fluid L or are submerged in the fluid L, the light emitted from the emission unit may reach the light-receiving unit. Thus, the third sensors S3 are disposed in consideration of the water surface of the fluid L according to a reference inclination range of the first cartridge 310 so that the first cartridge 310 can detect whether the first cartridge 310 is in the reference inclination range. The emission unit and the light-receiving unit are provided in separate positions above. However, even when the emission unit and the light-receiving unit are disposed in the same position, the light emitted from the emission unit are reflected on an inner wall surface of the first cartridge 310 and are applied to the light-receiving unit so that a similar principle to the above description can be implemented.

In an embodiment, the third sensors S3 may be disposed at an outer circumferential side of the inner upper surface of the first cartridge 310 as illustrated in FIG. 15. Thus, a change in heights of the third sensors S3 with respect to a change in inclination of the first cartridge 310 can be increased. As a result, the inclination of the first cartridge 310 can be more precisely detected.

When the first cartridge 310 is excessively inclined, there is the risk that ultrasonic waves may be applied in an undesired position. Thus, a procedural subject or the practitioner's body may also be injured. In particular, when the transducer 314 generates HIFU and forms the thermal lesion 12 at a predetermined position, the risk can be further increased.

In order to solve such a problem, the ultrasonic wave generating device 10 according to an embodiment of the present disclosure cuts off the generation of ultrasonic waves when the inclination of the first cartridge 310 deviates from a predetermined range.

That is, when the inclination of the first cartridge 310 is detected and the inclination of the first cartridge 310 deviates from the normal range as described above, the controller 150 may cut off power provided to the transducer 314 or may stop an ultrasonic wave generating operation of the transducer 314. Thus, a risk that may occur as the first cartridge 310 is excessively inclined can be reduced.

In particular, when ultrasonic waves are generated in a state in which the permeable member 318 of the first cartridge 310 is in an upward direction, the ultrasonic waves may be transmitted toward the practitioner or a procedural assistant and a dangerous situation may occur. In addition, when the amount of the fluid L filled in the first cartridge 310 is insufficient, that is, when the ultrasonic waves are emitted upward in this way, the permeable member 318 may be damaged. As a result, leakage of the fluid L may be increased or the first cartridge 310 may malfunction, and safety and reliability can be greatly lowered.

Figure 17:
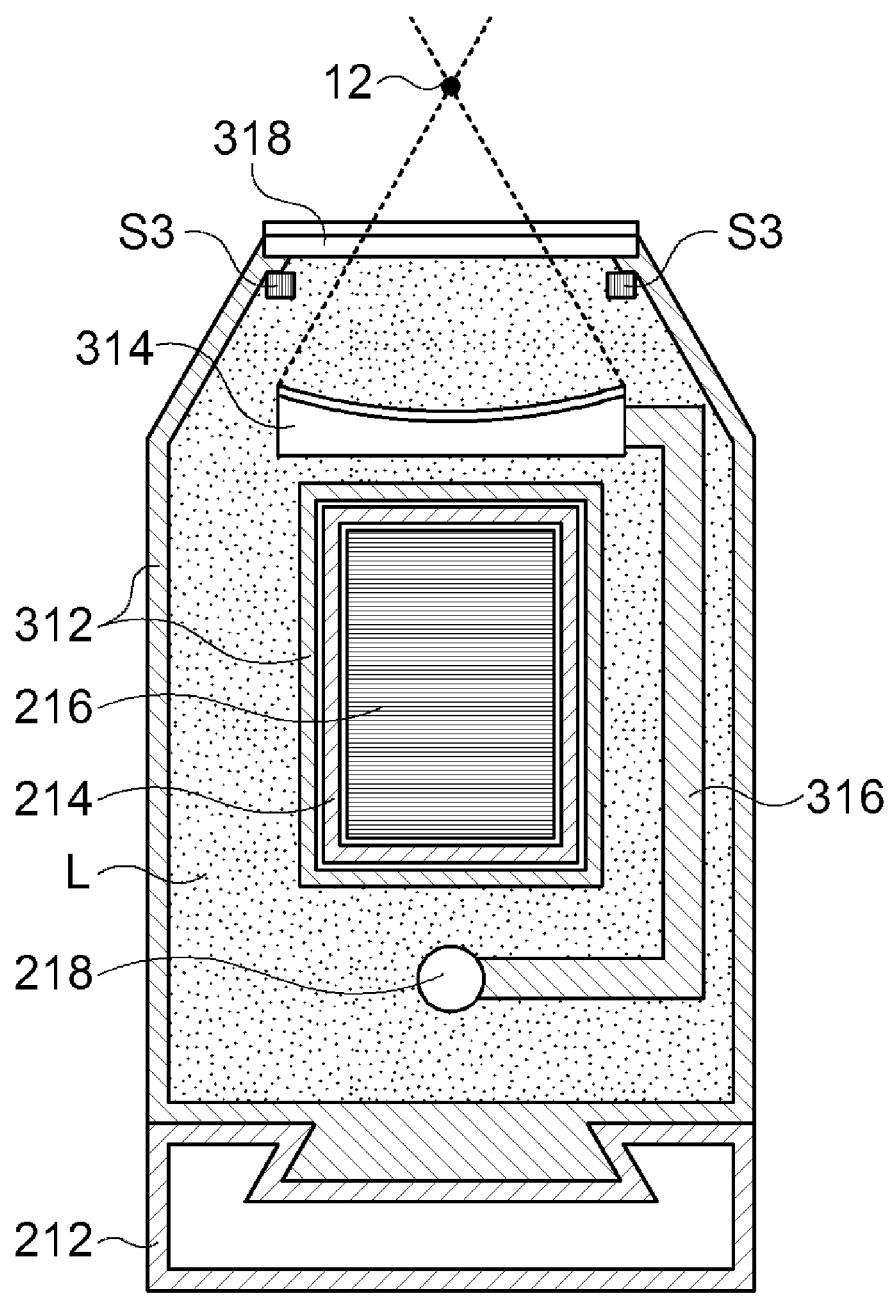
FIG. 17 is a cross-sectional view of a cut surface taken along line I-I' of FIG. 12 in an ultrasonic wave generating device according to another embodiment of the present disclosure.
Figure 18:
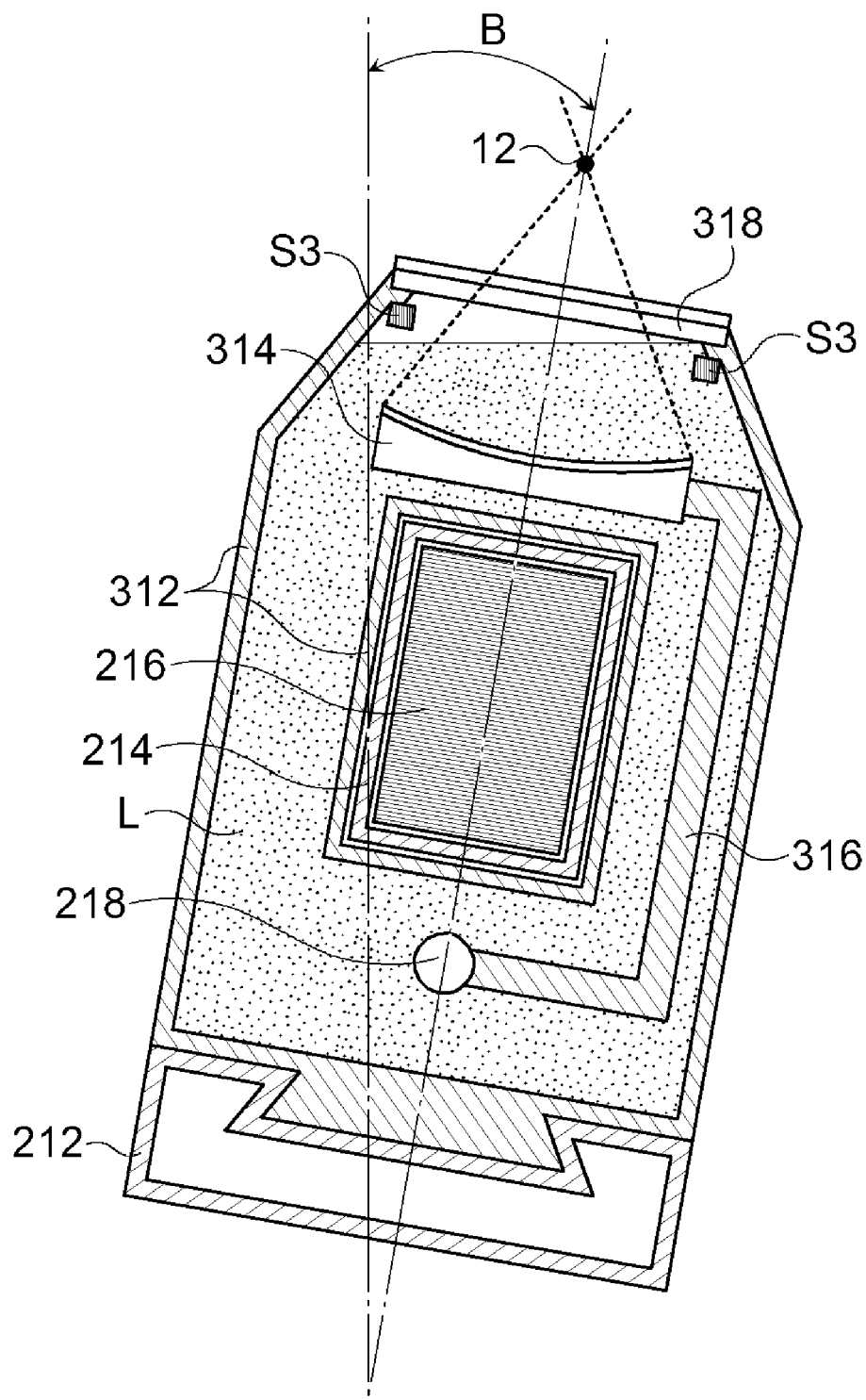
FIG. 18 is a view for explaining an operating principle of an ultrasonic wave generating device according to another embodiment of the present disclosure.

Here, referring to FIGS. 17 and 18, in an embodiment, each of the third sensors S3 may be disposed in a region between the permeable member 318 and the transducer 314 of the first cartridge 310. In this case, when the permeable member 318 of the first cartridge 310 is in a downward direction, the third sensor S3 cannot measure the amount of the fluid L or the inclination of the first cartridge 310. However, when the permeable member 318 of the first cartridge 310 is in the upward direction, the third sensor S3 may measure the amount of the fluid L. That is, when the third sensor S3 is not submerged in the fluid L, the abnormal state in which the amount of the fluid L is insufficient may be determined.

In addition, as described above with reference to FIGS. 14 to 16, the third sensors S3 may be disposed near the lower surface inside the first cartridge 310 even in the current embodiment. In addition, the plurality of third sensors S3 are spaced a predetermined distance apart from each other so that the inclination of the first cartridge 310 may be detected in a similar manner to that described above. Thus, the ultrasonic wave generating device 10 according to the current embodiment may detect a degree of inclination toward one side of the vertically upward direction in a state in which the permeable member 318 of the first cartridge 310 is in the upward direction. In this case, when the permeable member 318 of the first cartridge 310 is inclined a predetermined angle or less toward the one side of the vertically upward direction in the state in which the permeable member 318 of the first cartridge 310 is in the upward direction, a dangerous situation may occur as described above.

Thus, in one form, when the permeable member 318 of the first cartridge 310 is within an inclination range of approximately 10 degrees or less toward the one side of the vertically upward direction while being in the upward direction, ultrasonic wave generation of the transducer 314 is stopped.

Figure 19:
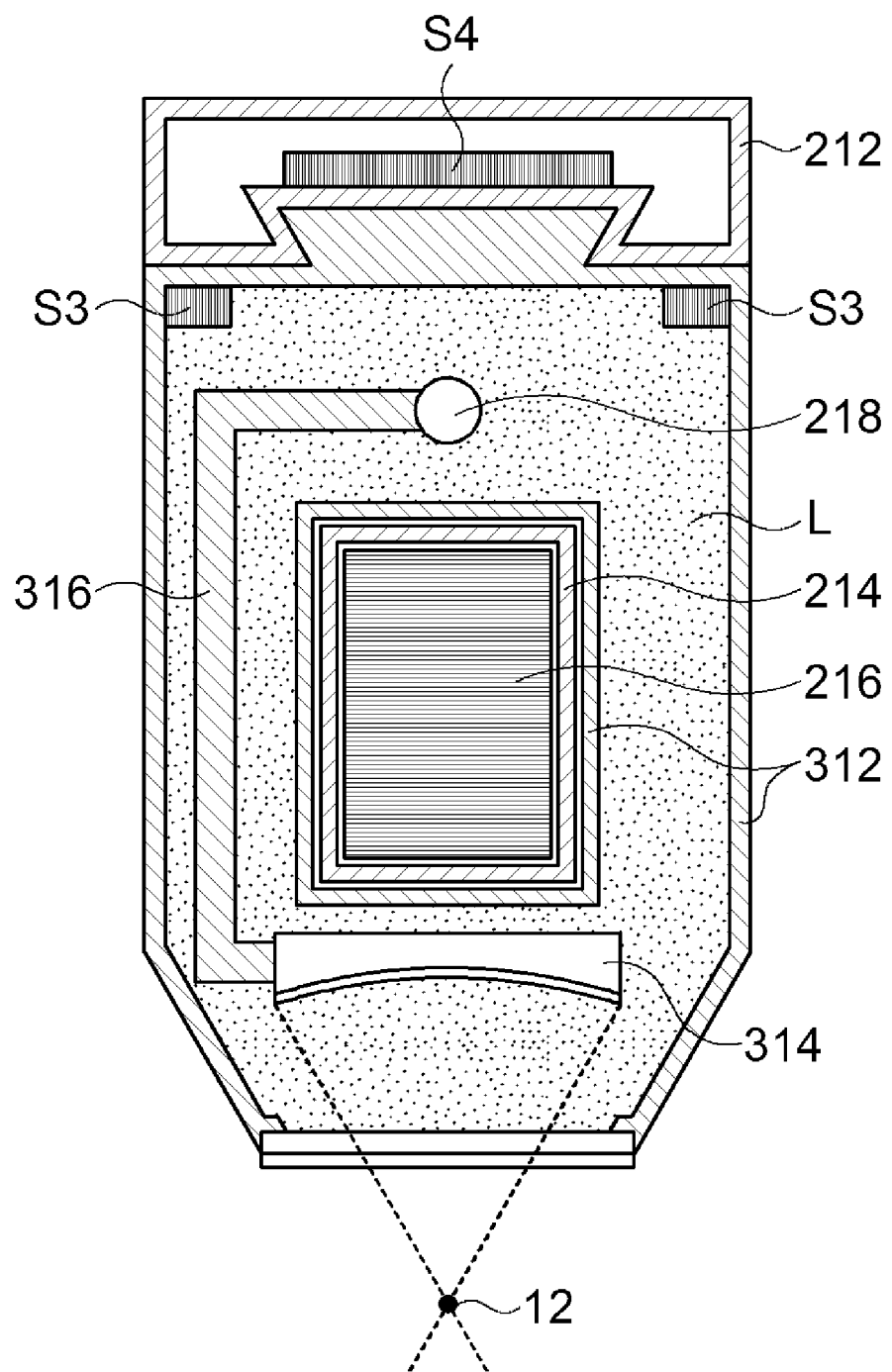
FIG. 19 is a cross-sectional view of a cut surface taken along line I-I' of FIG. 12 in an ultrasonic wave generating device according to another embodiment of the present disclosure.
Figure 20:
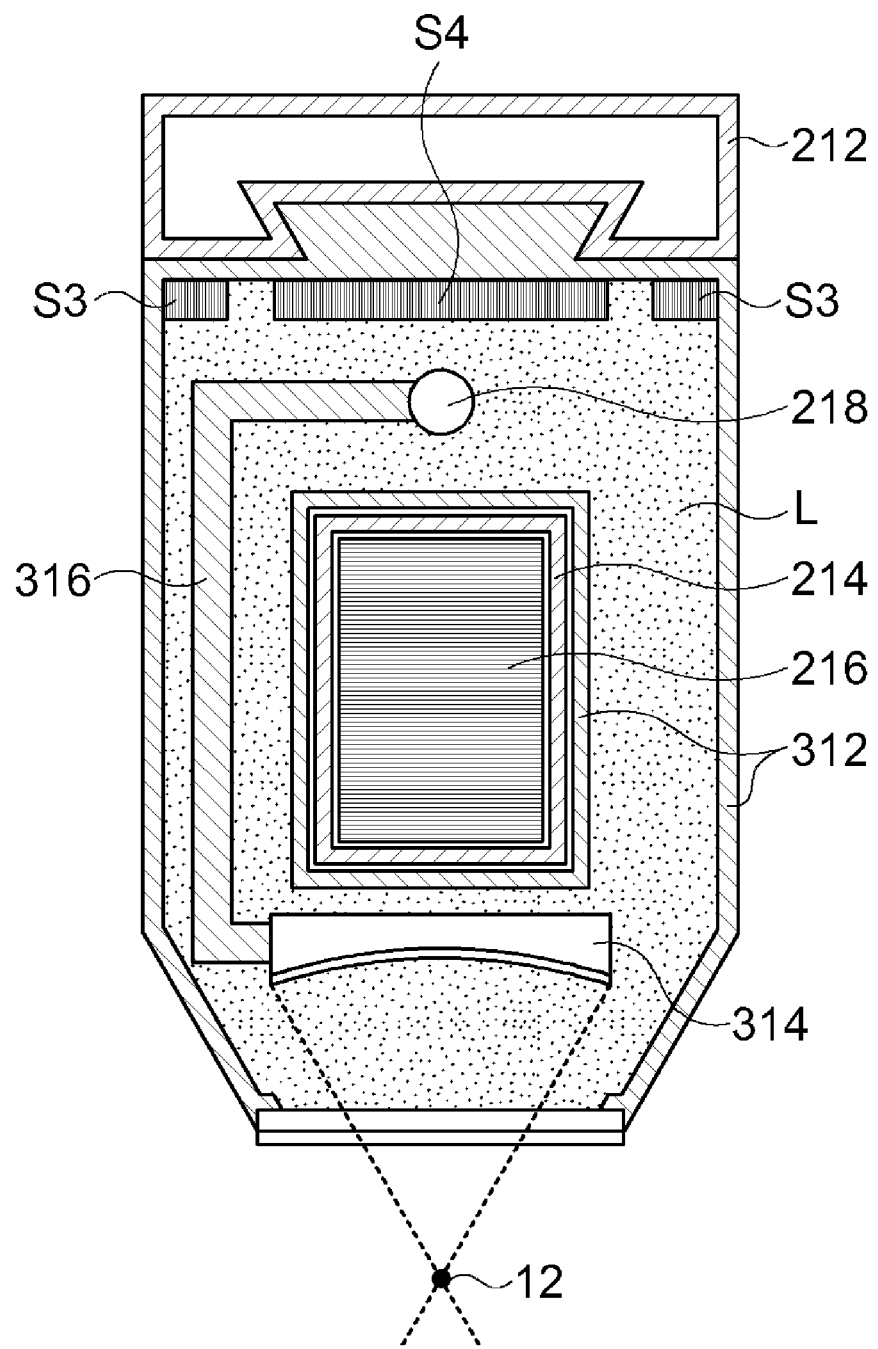
FIG. 20 is a cross-sectional view of a cut surface taken along line I-I' of FIG. 12 in an ultrasonic wave generating device according to another embodiment of the present disclosure.

Continuing to refer to FIGS. 19 and 20, the sensing means SM of the ultrasonic wave generating device 10 according to an embodiment of the present disclosure may include the fourth sensor S4. Here, the fourth sensor S4 may be a sensor that senses at least one of an inclination, an angular velocity, and an acceleration.

Here, the fourth sensor S4 may be implemented with a general tilt sensor, an acceleration sensor such as an inertia type sensor, a gyro type sensor, or a silicon semiconductor type sensor, or an angular velocity sensor. Principles or methods of these sensors are already well-known and thus detailed descriptions thereof will be omitted in the present specification.

Meanwhile, the fourth sensor S4 may be provided in the procedure handpiece 210 as illustrated in FIG. 9, or in a cartridge as illustrated in FIG. 20. Here, when the fourth sensor S4 is provided in the procedure handpiece 210, the fourth sensor S4 provided in the procedure handpiece 210 can be commonly utilized without the requiring the fourth sensor S4 to be provided in each of the above-described cartridge sets. The fourth sensor S4 may be connected to the controller 150, and the controller 150 receives a signal generated in the fourth sensor S4 so that the inclination of the cartridge may be monitored.

In another example, a relay that turns the transducer 314 on or off and a power supply line (not shown) may be connected to the fourth sensor S4 so that an ultrasonic wave generating operation can be stopped or performed rapidly according to the inclination. Thus, in comparison to the case in which the transducer 314 is controlled via the controller 150 software-implemented in an additional piece of hardware such as an equipment body, stopping or performing of the ultrasonic wave generation can be more rapidly adjusted through only a simple configuration.

Figure 21:
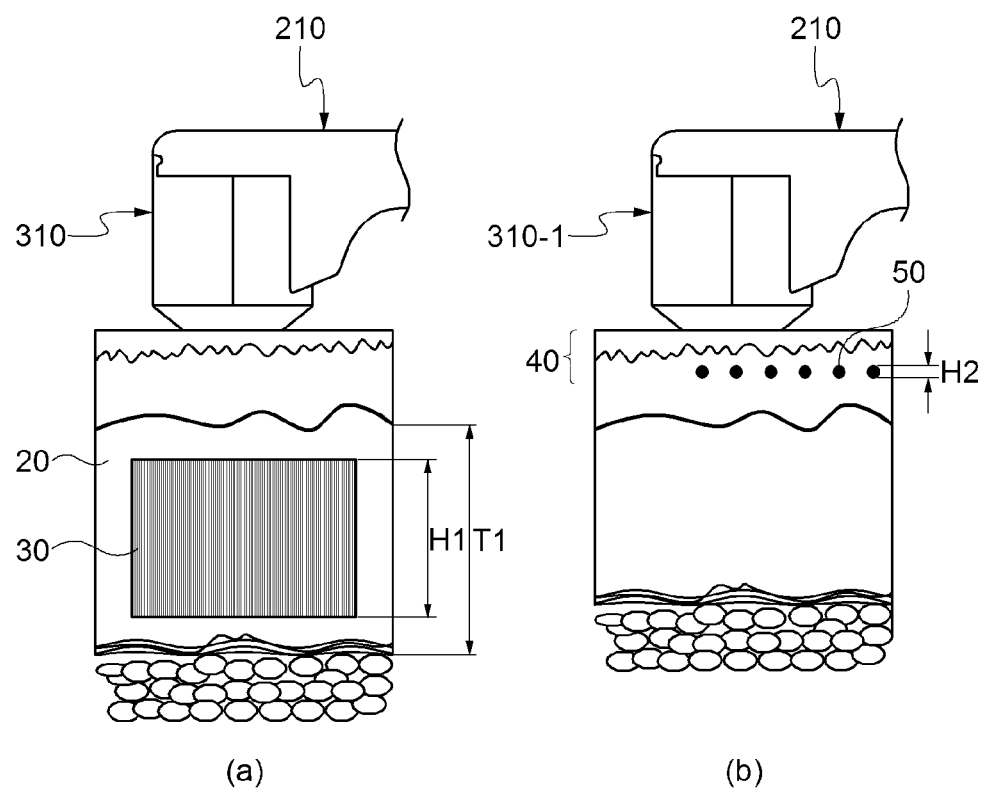
FIG. 21 is a view for explaining first and second cartridges according to an embodiment of the present disclosure.

Referring to (a) of FIG. 21, the first cartridge 310 according to an embodiment of the present disclosure may be used to perform a procedure for a reduction in a relatively-thick subcutaneous layer. In an embodiment, the first cartridge 310 may be used when a thickness T1 of a subcutaneous layer 20 which is a procedural subject is approximately 25.0 mm or more. That is, the first cartridge 310 may be set on a condition such that the procedure can be performed when the thickness T1 of the subcutaneous layer 20 is approximately 25.0 mm or more. In this case, the possibility that a procedural patient is an extremely obese patient may be high. The first cartridge 310 may be adjusted so that a radiation depth of HIFU from a surface of skin can be adjusted to be in a range of approximately 11.0 to 15.0 mm while a vertical length H1 of a HIFU lesion 30 is adjusted to be in a range of approximately 8.0 to 12.0 mm. When the vertical length H1 of the HIFU lesion 30 is less than approximately 8.0 mm, a reduction in efficiency of the subcutaneous layer 20 may be lowered. On the contrary, when the vertical length H1 of the HIFU lesion 30 exceeds approximately 12.0 mm, the HIFU lesion may be formed in a region that deviates from the subcutaneous layer 20. In addition, when the radiation depth is less than approximately 11.0 mm or exceeds approximately 15.0 mm during a procedure, the HIFU lesion 30 may deviate from the subcutaneous layer 20. Thus, when the vertical length H1 of the HIFU lesion 30 is adjusted to be approximately 10.0 mm±2.0 mm and the radiation depth of the HIFU is adjusted to be approximately 13.0 mm±2.0 mm, the transducer 314 of the first cartridge 310 can alleviate a risk that a procedure may be performed on a skin tissue other than the subcutaneous layer 20 even when the procedure is performed in a state in which the thickness T1 of the subcutaneous layer 20 is approximately 25.0 mm or more.

Here, the transducer 314 of the first cartridge 310 performs a forward or backward motion, that is, a rectilinear reciprocating motion, so that a plurality of HIFU lesions 30 can be generated. In this case, a distance between the plurality of HIFU lesions 30 may be in a range of approximately 0 or 1.0 mm or less so that the HIFU lesions 30 form a straight line or pillar shape without an intermediate cutoff and can thermally decompose the subcutaneous layer 20. However, because pain of a procedural subject may be large when the HIFU lesions 30 overlap, HIFU is ideally radiated as close as possible to the HIFU lesions 30 on a condition that the HIFU lesions 30 do not overlap.

Referring to (b) of FIG. 21, the second cartridge 310-1 according to an embodiment of the present disclosure may be used to perform a procedure for a reduction in a relatively thin subcutaneous layer compared to the above-described first cartridge 310. In an embodiment, the second cartridge 310-1 may be used when a thickness T2 of a subcutaneous layer 40, which is a procedural subject, is between approximately 7.0 mm and 25.0 mm. That is, the second cartridge 310-1 may be set on a condition that the thickness T2 of the subcutaneous layer 40 is smaller than approximately 25.0 mm and at least 7.0 mm. In this case, the possibility that the procedural patient is performed may be a morbidly obese patient, may be high. When a vertical length H2 of a HIFU lesion 50 is adjusted to be in a range of approximately 5.0 to 9.0 mm, a radiation depth of the HIFU from a surface of skin may be adjusted to be in a range of approximately 6.0 to 10.0 mm. When the vertical length H2 of the HIFU lesion 50 is less than approximately 5.0 mm, a reduction in efficiency of the subcutaneous layer 20 can be lowered. On the contrary, when the vertical length H2 of the HIFU lesion 50 exceeds approximately 9.0 mm, a HIFU lesion may be formed in a region that deviates from the subcutaneous layer 40. Also, when the radiation depth is less than approximately 6.0 mm or exceeds approximately 10.0 mm during a procedure, the HIFU lesion 50 may deviate from the subcutaneous layer 40. Thus, when the vertical length H2 of the HIFU lesion 30 is adjusted to be approximately 7.0 mm±2.0 mm and the radiation depth of the HIFU is adjusted to be approximately 8.0 mm±2.0 mm, the transducer 314 of the second cartridge 310-1 can alleviate the risk that a procedure is performed on a skin tissue other than the subcutaneous layer 40 even when the procedure is performed in a state in which the thickness T2 of the subcutaneous layer 20 is between approximately 7.0 mm and 25.0 mm.

Here, while the transducer 314 of the second cartridge 310-1 performs a forward or backward motion, that is, a rectilinear reciprocating motion, a plurality of HIFU lesions 50 may be generated. In this case, a distance between the plurality of HIFU lesions 50 may be approximately 0 or 1.0 mm or less so that the HIFU lesions 50 form a straight line or pillar shape without an intermediate cutoff and can thermally decompose the subcutaneous layer 40. However, because pain of a procedural subject may be large when the HIFU lesions 50 overlap, HIFU is ideally radiated to be as close as possible to the HIFU lesions 50 on a condition that the HIFU lesions 50 do not overlap.

An ultrasonic wave generating device and a procedure method using the same according to an embodiment of the present disclosure can be utilized in various procedures such as obesity treatments, skin care, and gynecological disease treatments.

The invention claimed is:
1. An ultrasonic wave generating device comprising:
a housing configured to seal an inside of a cartridge;
a transducer disposed in the housing and configured to generate ultrasonic waves;
a rotational force applying unit configured to receive a rotational force from an outside of the housing and perform a rotational motion;
a conversion unit configured to convert the rotational motion of the rotational force applying unit into a rectilinear motion and provide the rectilinear motion to the transducer;

a controller configured to control the transducer in generating the ultrasonic waves; and a position detection unit configured to detect a position of the transducer, wherein the position detection unit comprises:

a magnet unit provided in the transfer member or the transducer in the position detection unit; and a sensor provided in the cartridge to face the magnet unit and configured to detect a position of the magnet unit; and wherein the conversion unit comprises:

a driving joint connected to the rotational force applying unit and configured to rotate; and a driven joint fixed to the transducer and configured to perform the rectilinear motion forward and backward based on a rotational motion of the driving joint; and wherein the driving joint comprises:

a cylindrical cam having a cylindrical shape and having a first end coupled to the rotational force applying unit; and a groove portion having a spiral shape in a surface of the cylindrical cam;

and wherein the driven joint comprises:

a guide portion provided in parallel to a rotating shaft of the cylindrical cam;

a transfer member to perform the rectilinear motion along the guide portion; and a protrusion coupled to the guide portion and inserted into the groove portion of the cylindrical cam to perform the rectilinear motion according to a rotational motion of the cylindrical cam;

wherein the housing includes a concave groove;

wherein the cylindrical cam has a second end which has a shaft protrusion;

wherein the first end and the second end of the cylindrical cam are disposed at opposite ends; and wherein the shaft protrusion is inserted into the concave groove and the cylindrical cam is configured to be rotatably coupled to the housing.

2. The ultrasonic wave generating device of claim 1, further comprising an outer rotating unit disposed outside the housing and connected to the rotational force applying unit by magnetism.

3. The ultrasonic wave generating device of claim 1, wherein the controller is configured to control the transducer not to generate the ultrasonic waves based on a signal output from the position detection unit when the transducer is within a predetermined distance from a previous position at which the ultrasonic waves are generated.

4. The ultrasonic wave generating device of claim 1, further comprising another sensor configured to sense at least one of an amount of a fluid, an inclination of a surface of the fluid, or an inclination of the cartridge, wherein:

the fluid is used to transmit the ultrasonic waves;

the fluid is filled in the housing, and the controller is configured to control the transducer to stop generation of the ultrasonic waves when at least one of the amount of the fluid, the inclination of the surface of the fluid, or the inclination of the cartridge deviates from a predetermined range.

5. The ultrasonic wave generating device of claim 1, wherein:

a first side of the transfer member is fixed to the transducer; and a second side of the transfer member is inserted into the groove portion.

6. The ultrasonic wave generating device of claim 5, wherein the position detection unit further comprises:

another magnet unit provided in one of the cylindrical cam and the housing; and another sensor provided in the cartridge and configured to detect a position of the another magnet unit.

7. The ultrasonic wave generating device of claim 1, wherein the transfer member performs the rectilinear motion between a first reference point and a second reference point, the sensor is provided at a position facing the magnet unit when the transfer member is disposed at the first reference point, and the sensor is provided at a position facing the magnet unit when the transfer member is disposed at the second reference point.

8. A procedure method using an ultrasonic wave generating device, the method comprising:

performing a procedure by generating thermal lesions of high intensity focused ultrasound (HIFU) at a predetermined depth of a skin tissue in a noninvasive manner using the ultrasonic wave generating device of claim 1, wherein the transducer is moved between a first reference point and a second reference point;

sensing whether the transducer is within a predetermined distance from a previous position at which the HIFU is generated using the transducer while the transducer is moved between the first reference point and the second reference point; and controlling the transducer not to generate the HIFU when the transducer is within the predetermined distance from the previous position at which the HIFU is generated.

9. The method of claim 8, further comprising:

performing, by the transducer, the rectilinear motion between the first reference point and the second reference point by receiving the rotational motion of the cylindrical cam, and wherein the sensing of whether the transducer is within a predetermined distance from the previous position at which the HIFU is generated using the transducer is performed by detecting a rotation degree of the cylindrical cam.

10. The method of claim 8, further comprising, when the transducer is disposed at the first reference point or the second reference point, stopping movement of the transducer.

11. The method of claim 8, further comprising adjusting a distance between the thermal lesions by controlling a rotational speed of the cylindrical cam, wherein the transducer is configured to perform the rectilinear motion between the first reference point and second reference point by receiving the rotational motion of the cylindrical cam.

* * * * *